United States Patent [19]

Yamamoto et al.

[11] Patent Number: 5,408,307
[45] Date of Patent: Apr. 18, 1995

[54] CELL ANALYZER

[75] Inventors: Koji Yamamoto; Masahiro Hanafusa, both of Kyoto; Michio Nishimura, Osaka; Yoshihiro Nakatsuji, Kyoto; Fumio Onuma, Kyoto; Shinichi Hirako, Kyoto; Kunio Kaede, Shiga, all of Japan

[73] Assignee: Omron Tateisi Electronics Co., Kyoto, Japan

[21] Appl. No.: 377,930

[22] Filed: Jul. 11, 1989

[30] Foreign Application Priority Data

| Jul. 11, 1988 | [JP] | Japan | 63-172096 |
| Jul. 29, 1988 | [JP] | Japan | 63-191538 |
| Aug. 1, 1988 | [JP] | Japan | 63-193072 |
| Aug. 2, 1988 | [JP] | Japan | 63-193033 |
| Aug. 12, 1988 | [JP] | Japan | 63-202410 |

[51] Int. Cl.$^6$ ............. G01N 21/00; C12Q 1/00
[52] U.S. Cl. ............. 356/73; 356/39; 356/336; 435/724; 435/30; 435/34; 435/39; 436/10; 436/52
[58] Field of Search ............. 356/73, 39, 335–339, 356/343, 318, 364, 36; 250/201 AF; 364/400, 413.07, 413.08; 436/10, 52; 435/7.24, 30, 34, 39

[56] References Cited

U.S. PATENT DOCUMENTS

| 3,883,247 | 5/1975 | Adams | 356/39 |
| 4,325,483 | 4/1982 | Lombardo et al. | 364/413.08 |
| 4,661,913 | 4/1987 | Wu . | |
| 4,662,742 | 5/1987 | Chupp | 356/73 |
| 4,690,561 | 9/1987 | Ito | 356/73 |
| 4,747,685 | 5/1988 | Suzuki | 356/336 |
| 4,751,179 | 6/1988 | Ledis et al. | 356/36 |

FOREIGN PATENT DOCUMENTS

| 0135984 | 4/1985 | European Pat. Off. . |
| 62-134559 | 6/1987 | Japan . |
| 63-191043 | 8/1988 | Japan . |

OTHER PUBLICATIONS

IEEE Transactions on Computers, vol. C-26, No. 9, Sep. 1977, pp. 882–894; M. Yachida et al., "A Versatile Machine Vision System for Complex Industrial Parts".
Cytometry, vol. 1, No. 5, 1981, pp. 325–336; G. C. Salzman et al., "Modular Computer Programs for Flow Cytometry and Sorting: The Lacel System".
The Journal of Histochemistry and Cytochemistry, vol. 24, No. 1, 1976, pp. 308–314; G. C. Salzman et al., "Gynecologic Specimen Analysis by Multiangle Light Scattering in a Flow System".
Clinical Chemistry, vol. 18, No. 8, 1972, pp. 738–788; A. M. Saunders, "Development of Automation of Differential Leukocyte Counts by Use of Cytochemistry".
Cytometry-The Journal of the Soc. for Analytical Cytology, vol. 9, No. 4, Jul. 1988, pp. 405–408, New York, N.Y., US, Y. Kosugi et al., "An Interactive Multivariate Analysis of FCM Data".

*Primary Examiner*—Hoa Q. Pham
*Attorney, Agent, or Firm*—Fish & Richardson

[57] ABSTRACT

In a cell analyze apparatus, a light beam is irradiated onto cells (or particles like the cells) flowing through a flow cell so as to measure cell light information for each cell with respect to a plurality of parameters (for example, the forward scattered light intensity, the right angle scattered light intensity and the intensity of fluorescence by different dye). Based on a minimal point of a histogram associated with the cell light information with respect to one or more parameters, the cell population is subdivided into fractions. When the minimal point is missing in the histogram, the parameters above are converted by use of a predetermined conversion expression (for example, a coordinate conversion is effected on the parameters) such that a minimal point is detected from the histogram of cell light information related to the new parameters obtained by the conversion, thereby subdividing an objective cell population.

13 Claims, 22 Drawing Sheets

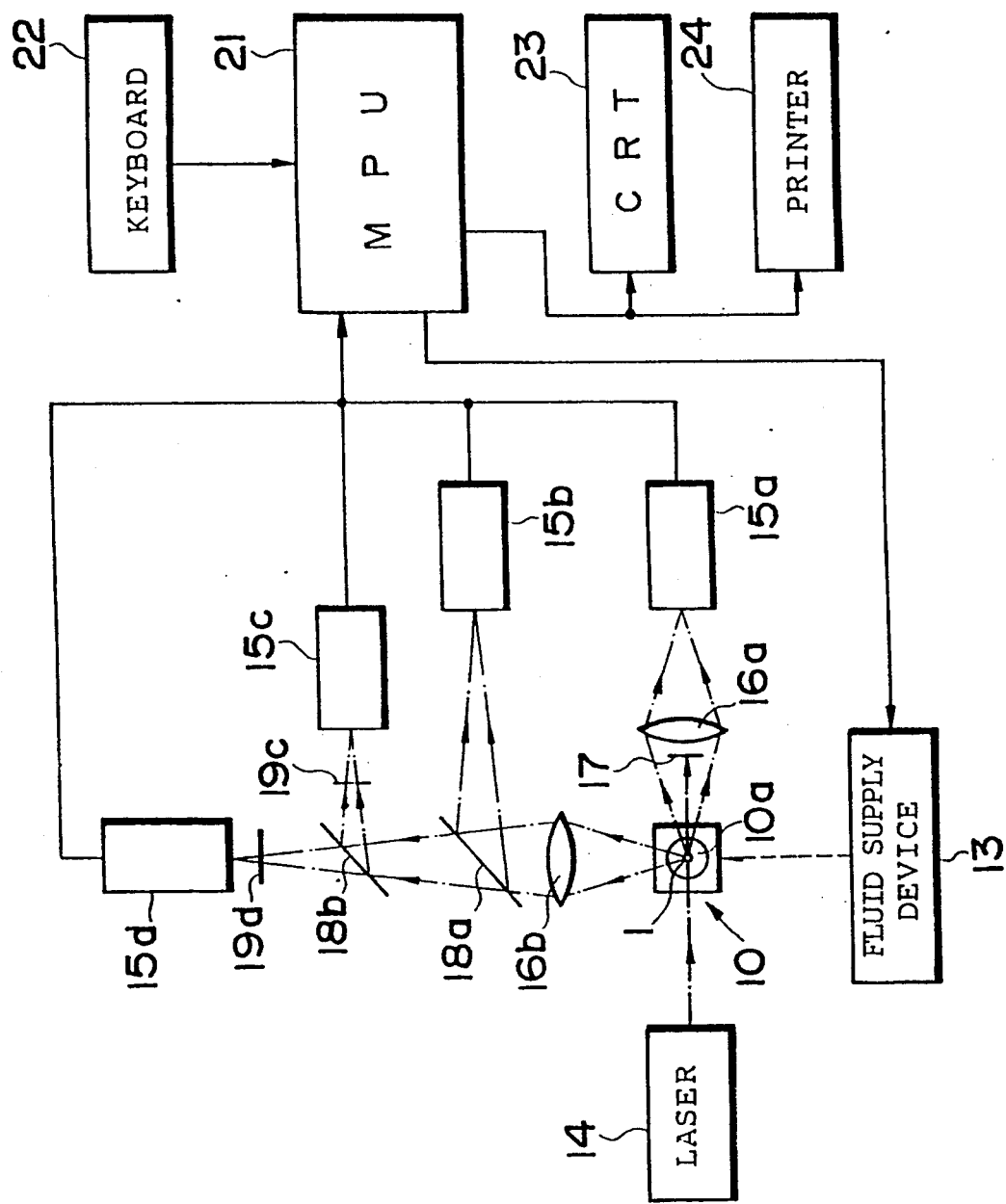

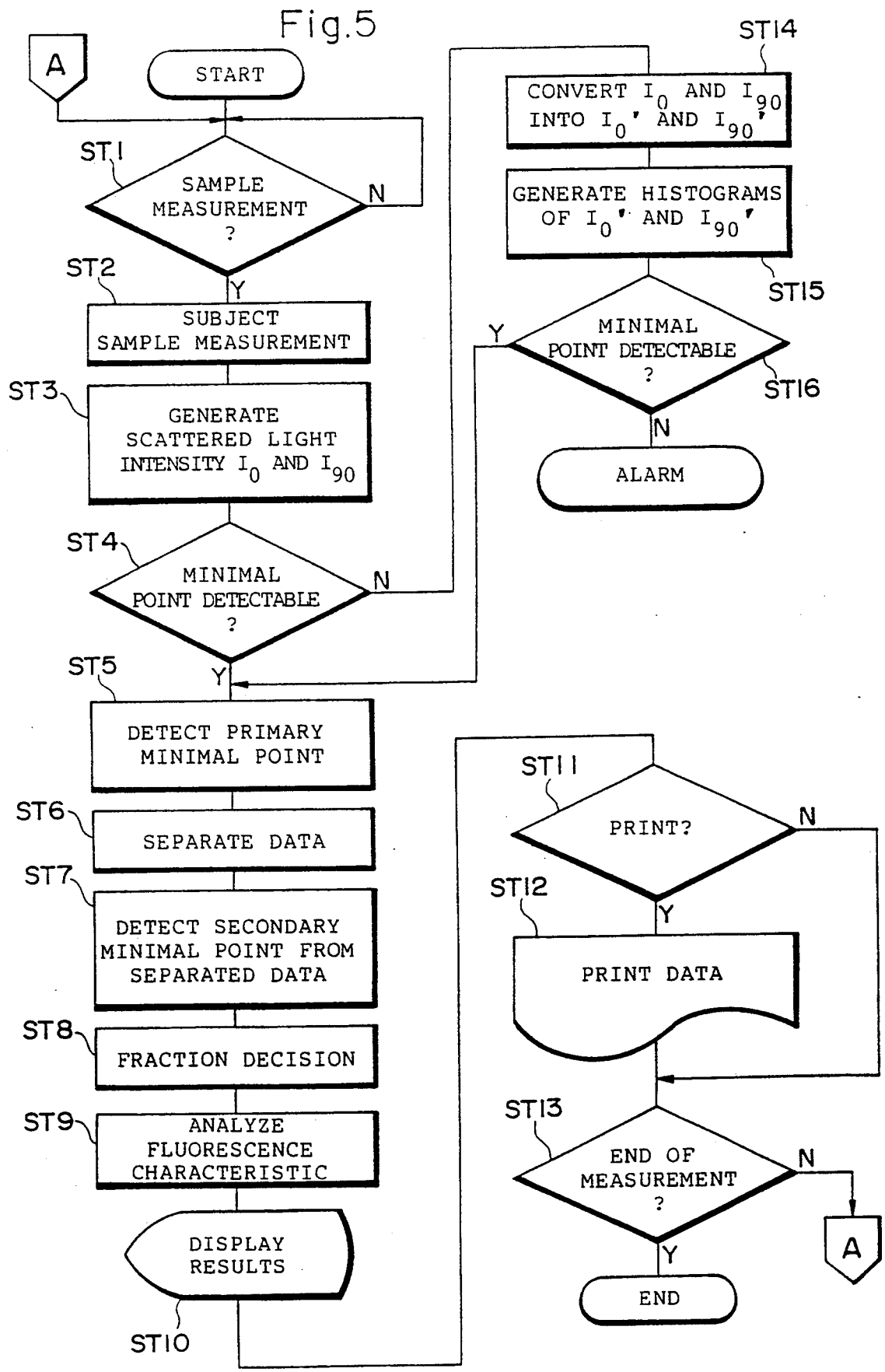

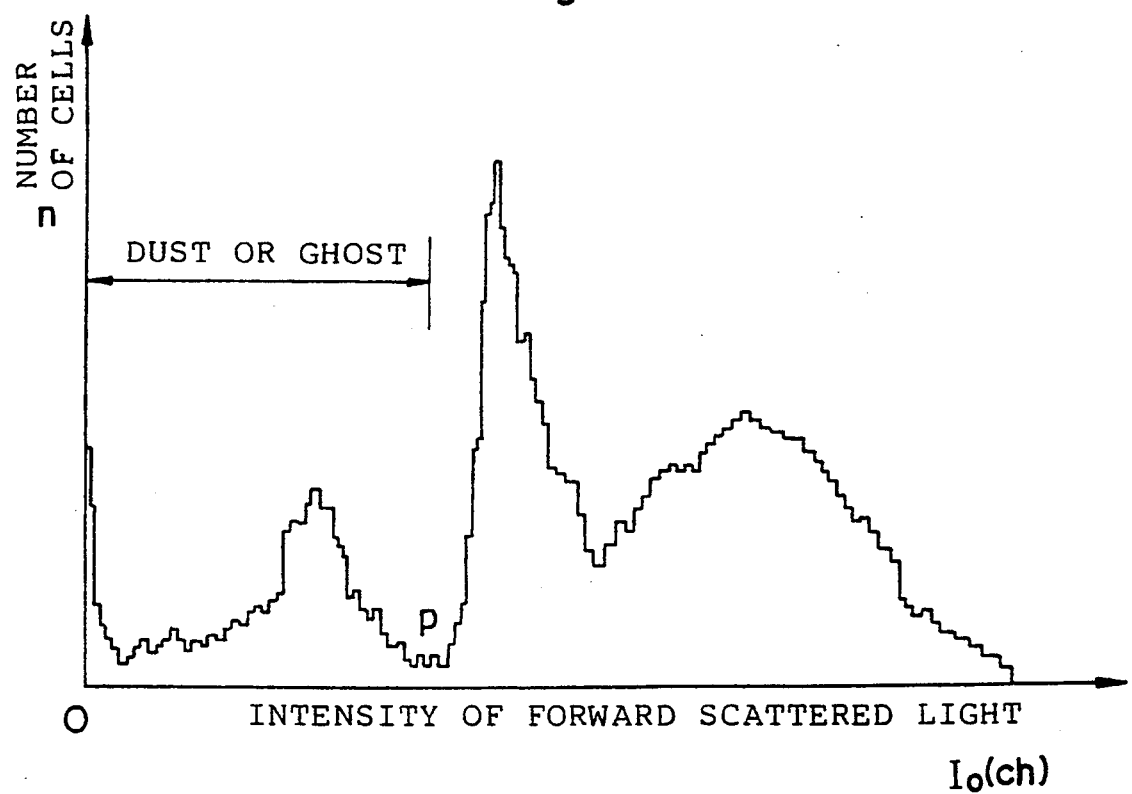

CELL ANALYZER

BACKGROUND OF THE INVENTION

1. Field of the invention

The present invention relates to an apparatus for analyzing cells by means of flow cytometry.

2. Description of the Prior Art

In flow cytometry, a sample including cells (or particles like cells) conjugated, for example, by use of fluorescent dye or antibodies is passed together with sheath fluid into a crystal flow cell. The sample is wrapped in a pressurized sheath flow so that a thin, stable stream of the sample (laminar flow) flows through the center of the flow cell (hydro-dynamic focusing). The cells line up within stream and the flow past a focused laser beam (the sensing zone) at a constant speed. At this point, scatter lights and fluorescence from the cells are measured simultaneously by some independent sensors. The computer analyses the strength of these signals and uses it to classify the cells.

As cell analyzer by flow cytometry, there has been known an apparatus including a flow cell for producing a thin stream, a light source (for example, a laser device) to apply a light beam onto cells flowing through the flow cell, a sensor or detector for detecting light information of cell on which the light beam is irradiated so as to convert the information into electric signals, and a computer achieving operations such as an analysis process of the light information of the cells thus represented in the form of electric signals.

In this cell analyze apparatus of the prior art, a sample in which cells conjugated a fluorescent dye or antibodies are floating is supplied into the flow cell together with sheath fluid. A sheath flow is then formed in the flow cell such that owing to the hydro-dynamic focusing effect, the cells are arranged in a line along a center axis of the flow cell.

When a light beam is applied onto the cells, there are developed scatter lights and fluorescence such that the intensity of the lights and fluorescence are detected as parameters constituting the cell light information by means of light detectors such as a photoelectric multiplier.

Incidentally, there exists a case in which cell analysis is desired to be effected on one cell population selected from a plurality of cell populations included in the sample. For example, in a case of an analysis to be conducted on lymphocyte subsets or phagocytosis of human blood cells, whole blood is employed as a sample. That is, in this situation, incubated with a monoclonal antibody conjugated with a fluorescent dye [in a case of two-color analysis, for example, an OKT4 monoclonal antibody conjugated with fluorescenin isothiocyanate (FITC; green fluorescence) and an OKT8 monoclonal antibody conjugated with phycoerythrin (PE; red fluorescence)] After it is caused to react upon whole blood so as to be thereafter subjected to hemolysate a sample is thereby prepared.

The laser beam is irradiated onto each cell flowing through the flow cell so as to detect by means of detectors which measure four parameters, namely, an intensity of forward light scattering $I_0$ (of scatter light in a direction along the optical axis of the radiated beam), an intensity of 90° or right angle light scattering (of scatter light in a direction orthogonal to the optical axis of the radiated laser beam), an intensity of green fluorescence $I_g$, and an intensity of red fluorescence $I_r$, thereby obtaining light information of the cell (to be called cell light data in some cases). The sample includes, in addition to lymphocytes, other substances such as monocytes and granulocytes and hence it is necessary to discriminate the data related to lymphocytes from other cells.

For this purpose, there has been known a method called a window method in which the cell light information associated with a desired cell population is discriminated and is gathered. (For details, refer to the Japanese Patent Unexamined Publication (Kokai) No. 62-134559, for example.) According to the window method, in a space including a coordinate system constituted with one or more parameters selected from the light information items of the cells, the operator establishes an analysis region or area called a window such that light information of the cells belonging to the area is collected as the light information of the objective cell population.

For example, in lymphocyte subset analysis, there are adopted two parameters including the intensity of forward light scattering $I_0$ to represent cell size and the intensity of right angle light scattering $I_{90}$ to indicate complexity of cell internal matter so as to draw a cytogram in which the abscissa and the ordinate designate the values of $I_{90}$ and $I_0$, respectively. In this diagram, the values of $I_{90}$ and $I_0$ are normalized depending on the maximum values measured so as to set a maximum value of the scale to 256 (eight bits). The values are represented in the unit of channels (ch); moreover, b, c, and d respectively designate distributions of lymphocytes, monocytes, and granulocytes, respectively. In the graph, a stands for a distribution of debris, which includes substances such as membrane components of red blood cell and is usually removed at the noise threshold.

For analysis of lymphocytes, a reference sample (a sample of a person of a normal health) is employed so as to set a window e as indicated by double-dot-and-dash lines in FIG. 1. Data related to lymphocytes associated with the window e is selected (extracted) from the data gathered through the measurement. The data thus selected for lymphocytes is subjected to computations of the intensity $I_g$ and $I_r$ of the green and red fluorescence, respectively so as to attain the positive ratios of the reaction with a monoclonal antibody conjugated with a fluorescent dye such that the results are displayed on the CRT or are printed out on a sheet of paper by means of the printer.

However, according to the window method above, it is necessary in some cases for the operator to change the window depending on a sample so as to collect the light information of the objective cell population. For example, in lymphocyte subset analysis, since the location, size, and contour or shape of the distribution b of lymphocytes shown in FIG. 1 vary depending on the sample, the operator is required to change the window e in a corresponding fashion. Such a change of window prevents an automatic measurement of a great number of samples from being conducted with high efficiency.

In order to cope with such a difficulty, the present applicant has already filed an application of an automatic cell analyze apparatus in which the measurement is automatically carried out without necessitating the operator to establish the window (Japanese Patent Application No. 62-22884: Kokai No. 63-191043). In accordance with the cell analyzer above, one or more parameters selected from the cell light information items are employed to generate histograms such that minimal points (associated with the smallest frequency value in the distribution) are detected from the histograms so as to subdivide the cell populations to establish an analysis area including one or more subdivided regions or partitions, thereby collecting light information of cells belonging to the analysis area as the light information of the objective cell population. In this description, the minimal point does not indicate a minimal point defined in a sense of mathematics, namely, indicates a portion of a valley appearing between adjacent peaks in the frequency distribution.

For example, in the case of the lymphocyte subset analysis, as can be seen from FIGS. 2a and 2b, there are produced histograms associated with the intensity of right angle light scattering $I_{90}$ forward light scattering $I_0$ in which the ordinate designates the number $\underline{n}$ of cells. There are detected minimal points $p_1$, $p_2$, and $p_3$ of the histogram of I and minimal points $p_4$ and $p_5$ of the histogram of $I_0$. These minimal points $p_1$ to $p_5$ are represented in a cytogram related to $I_{90}$ and $I_0$ so as to obtain partitions or fractions indicated with broken lines in FIG. 1. Since the distribution of lymphocytes is included in the fraction B, there are retrieved, from the light information items of all the measured cells, light information items of cells belonging to the fraction B, namely, of cells for which $I_{90}$ is at least $p_1$ and at most $p_2$ and for which $I_0$ is at least $p_4$ and at most $p_5$, thereby collecting the light information of lymphocytes.

However, depending on samples, particularly, in a case of blood of a patient, there cannot be extracted any expected minimal points from the histograms produced with respect to one or more parameters above and hence the light information of the objective cell population cannot be attained in some cases. For example, in the lymphocyte subset analysis, there exists sometimes such case that the above minimal points $p_a$ or $p_1$ cannot be detected in a histogram of the intensity of right angle light scattering $I_{90}$ depending on conditions, histograms of such case being shown in FIGS. 8a and 8b which will be described later.

On the other hand, even if such minimal points are detected and there is determined a fraction containing the objective cell population, it is required to retrieve data items of all the measured cells by use of the two parameters so as to gather the light information of the objective cell population, which leads to a problem that a considerably long period of time is necessary for the data collect processing.

On the other hand, in the cell analyze apparatus of the prior art above, cell light information collect means gathers the light information of the objective cell population. However, as shown in FIG. 1, the fraction is a region having a rectangular shape in the cytogram; in consequence, the fraction is not completely matched with the shape or contour of the distribution of the objective cell population and hence light information of unnecessary cells are included in the attained light information of the objective cell population, namely, there arises a problem that the analysis precision is lowered.

As a method to determine an analysis area more suitably matched with the contour of the distribution of the objective cell population, there has been known the contour trace method, which however requires a long period of computation time and hence is not suitable with respect to the efficiency of the cell analysis.

Generally, the sample includes, in addition to the cells, other substances such as dust and dirt in a small amount; furthermore, the sheath fluid also includes a slight amount of dust. When such dust passes through the flow cell, unnecessary information, namely, a noise appears in the cell light information. For example, in a case of lymphocyte subset analysis, as shown in FIG. 3a, substances such as membrane components of erythrocytes remained in the sample as a result of hemolysis may appear as a ghost (debris) a as described above, or the dust in the sample or sheath fluid may be detected as a noise $\underline{ni}$.

To overcome this difficulty, in the cell analyze apparatus of the prior art, there is disposed a noise threshold circuit in a signal processing circuit to process signals supplied from the light detectors or photosensors such that the noise threshold levels Nh and Ns are established as shown in FIGS. 3a and 3b so as to remove the ghost a of red blood cell and the noise $\underline{ni}$ due to the dust, thereby guaranteeing the reliability of the cell analysis. In order to set the noise threshold values, the operator inputs threshold levels to the computer, which in turn transfers the received levels to the noise threshold cirucit. Namely, the computer operates only as an interface between the operator and the noise threshold circuit; in other words, in the conventional cell analyzer, it can be considered that the noise is removed by means of the hardware system.

In this situation, however, in a case where a great amount of samples are to be processed in a sequential fashion, for example, when an automatic sampler or an auto-sampler automatically supplying samples is used, due to the ghost of red blood cell and the dust in the sheath fluid, there is frequently required an operation to rearrange the noise threshold levels again, which leads to a problem that the efficiency of the inspection is reduced. In addition, if the change of the setting of the noise threshold levels is mistakenly ignored or if the setting change is inappropriately achieved, there arises a problem that the reliability is lowered in the cell analysis.

Recently, in the cell analyze apparatus above, in order to measure a large amount of samples efficiently, there has been considered an introduction of a so-called auto-sampler, which automatically supplies samples to the measurement system. Furthermore, with a provision of the auto-sampler, a direct contact can be avoided between the samples and the operator, which is favorable with respect to the prevention of bio-hazard.

However, there exist many factors exerting influences onto the positive ratio and hence the measurement conditions vary among the sample processing methods. For example, since the reaction between the various monoclonar antibodies and cells characterizes the results measurement, even when the identical detector is employed, the measurement cannot be conducted by use of the same detection gain. Moreover, due to the difference among the types of linkages between the monoclonal antibodies and fluorescent materials, there is required a correction to be effected when an intensity of the fluorescence is detected.

In consequence, for each sample, it is necessary to select and to set an appropriate measurement condition; however, the selection and setting operation requires knowledge gathered through a long experiece, and hence, conventionally, the operator achieves the select and set operation while monitoring the data. This job however necessitates an experienced skill and a considerable volume of labor; in consequence, the reliability of measured results cannot be increased and a great amount of samples cannot be efficiently subjected to the measurements. As a result, even if the auto-sampler is adopted so as to automatically conduct only the operation to supply the samples, the operation to select and to set the measurement condition is kept unchanged like in the case of the conventional system, and hence it is impossible to increase the efficiency of the measurements and to improve the the reliability of measured results.

SUMMARY OF THE INVENTION

It is therefore an object of the present invention to provide a cell analyzer in which even when a minimal point cannot be extracted from a histogram, the light information can be collected for the objective cell population and the information collection speed can be increased, thereby removing the problems above.

Another object of the present invention is to provide a cell analyze apparatus in which a fraction matching with a distribution of the objective cell population can be determined in a short period of processing time.

Still another object of the present invention is to provide a cell analyzing device in which appropriate noise threshold levels can be automatically established for each sample.

Another object of the present invention is to provide a cell analyze apparatus in which an optimal measurement condition can be automatically set for each sample so as to increase the reliability of measured results and to measure a great number of sample with highly efficiency.

The present invention is applicable to a cell analyze apparatus comprising a flow cell in which a cell float fluid including floating cells (also including particles like cells) flows, a light source for irradiating a light beam onto cells flowing through the flow cell, cell light information detect means operative for each cell onto which the light beam is irradiated for detecting cell light information with respect to a plurality of parameters, cell population subdivide means subdividing a cell population in the cell float fluid based on one or more parameters attained by the cell light information means, cell light information collect means for collecting cell light information of an objective cell population from cell light information detected by the cell light information detect means based on one or more fractions selected from the fractions obtained by the cell population subdivide means, cell light information process means for processing cell light information of the objective cell population collected by the cell light information collect means, and output means for outputting results of the processing effected by the cell light information process means.

According to the present invention, there is provided an apparatus including parameter convert means for converting one or more parameters by use of a predetermined conversion expression wherein the cell population subdivide means detects minimal points from histograms associated with cell light information with respect to the new parameters attained through the conversion conducted by the parameter convert means so as to subdivide into fractions the cell population based on the minimal points.

Referring now to an example of an analysis of lymphocyte subset, description will be given of the operation of the cell analyze apparatus with reference to the graph of FIG. 9. In this diagram, there is schematically shown a cytogram with the abscissa and the ordinate respectively representing the intensity $I_{90}$ of right angle scattered light and the intensity $I_0$ of forward scattered light. In a case where a minimal point cannot be detected in a histogram associated with $I_{90}$ or $I_0$, there may exist a possibility that in histograms associated with $I_{90}'$ and $I_0'$ obtained by rotating the axes of $I_{90}$ and $I_0$, for example, by an angle $\theta$, a minimal point can be detected so as to determine a fraction or a region B' including the distribution of lymphocytes.

Naturally, the conversion of $I_{90}'$ and $I_0'$, namely, the conversion of parameters are not limited to the simple rotation. An expression to be used for the conversion is optimized so that a minimal point can be easily detected in a histogram associated with the converted parameters.

Since the cell analyze apparatus according to the present invention includes the parameter convert means for converting one or more parameters by use of a predetermined conversion expression and is characterized in that the cell population subdivide means detects a minimal point from a histogram of the cell light information related to the new parameters converted by the parameter convert means, even if any minimal point cannot be detected from the histograms, it is possible to detect minimal points from histograms associated with the new parameters thus attained through the conversion, thereby advantageously collect the cell light information of the objective cell population.

In addition, the cell analyzer according to the present invention includes cell light information separate means charaterized in that the cell light information separate means separates cell light information of a cell population belonging to said one or more fractions with respect to a parameter from the cell light information detected by the cell light information detect means and that the cell light information collect means processes the separated cell light information so as to collect cell light information of a cell population belonging to one or more fractions with respect to other parameters.

In consequence, since the processing is not effected by retrieving the cell light information of all cells for each of the parameters, which is the case of the conventional system; the processing can be achieve at a higher speed.

Furthermore, according to the present invention, there is provided an apparatus comprising maximum frequency point extract means for processing cell light information of an object cell population collected by the cell light information collect means so as to extract a maximum frequency point on a cytogram of parameters associated with fractions of the cell population, direct line produce means for radially drawing on the cytogram direct lines from the maximum frequency point extracted by the maximum frequency point extract means, boundary point extract means for extracting boundary points based on histograms associated with the respective direct lines produced by the direct line produce means, and second cell light information collect means for linking the boundary points extracted by the boundary point extract means so as to form an area as a final fraction, thereby collecting cell light information of the objective cell population based on the final fraction.

Referring now to FIGS. 14 and 15a to 15c associated with the embodiment, description will be given of the cell analyze device according to the present invention.

For the partition B attained by the cell population subdivide means, the cell light information collect means gathers cell light information of an objective cell population, and then a maximum frequency point q is extracted from the cytogram (FIG. 14) so as to radially draw direct lines $l_1$ to $l_{12}$ from the point q. Histograms on these lines $l_1$ to $l_{12}$ are attained as shown in FIGS. 15a, 15b, and 15c. Assuming here points where the histograms intersect a predetermined threshold value or minimal points x of the histograms to be boundary points r, the boundary points $r_1$ to $r_{12}$ on the respective direct lines $l_1$ to $l_{12}$ are linked to each other so as to obtain a fraction B'' more suitably matched with with the distribution of the objective cell population. If the light information of the objective cell population is gathered depending on the fraction thus determined, the light information related to unnecessary cells or the like is not included in the resultant light information, which hence possibly improves the accuracy of the cell analysis.

In consequence, according to the present invention, a fraction more suitably adaptive to the objective cell population can be established in a reduced period of time, which leads to an advantage that the cell analysis is conducted with a higher precision.

Moreover, the apparatus in accordance with the present invention includes histogram generate means for processing the cell light information collected by the cell light information collect means to produce, for each predetermined frequency of a parameter, a histogram associated with another parameter, boundary point extract means for extracting boundary points by use of the histogram produced by the histogram generate means, and second cell light information collect means for linking the boundary points extracted by the boundary point extract means so as to form an area as a final fraction, thereby collecting cell light information of the objective cell population based on the final fraction.

Referring now to FIGS. 17, 18a, and 18b associated with the embodiment, description will be given of the cell analyzer according to the present invention. For the partition B established by the cell population subdivide means, the cell light information collect means effects a collection of the light information associated with an objective cell population, so that the histogram generate means processes the collected cell light information so as to create, for a predetermined frequency $\Delta I_0$ of a parameter $I_0$, a histogram related to another parameter $I_{90}$. The boundary point extract means extracts as boundary points $r_{ai}$ and $r_{bi}$, for example, the points where the histograms intersect the threshold value $m_{th}$ or the minimal points $y_1$ and $y_2$ of the histograms (FIGS. 18a, 18b). These boundary points are linked with each other so as to form a region B''', which more suitably matches with the objective cell population as compared with the fraction B previously obtained. In consequence, when the light information of the objective cell population is collected by use of the fraction thus determined, the light information related to unnecessary cells or the like is not included in the obtained light information, thereby improving the accuracy of the cell analysis.

Consequently, in accordance with the present invention, a fraction further suitably adaptive to the objective cell population can be established in a shorter period of time, which leads to an advantage that a higher precision is developed in the cell analysis.

Furthermore, the apparatus in accordance with the present invention includes histogram generate means for processing the cell light information collected by the cell light information collect means to produce a histogram related to the cell light information at least with respect to a parameter, minimal point detect means for detecting a minimal point in the histogram created by the histogram generate means, and unnecessary information remove means for establishing a noise threshold based on the minimal point detected by the minimal point detect means so as to remove by use of the noise threshold unnecessary information (a noise) contained in the cell light information detected by the cell light information detect means.

Referring now to FIGS. 22 and 3b associated with an example of an analysis of lymphocyte subset, description will be given of the operation of the cell analyze apparatus according to the present invention. FIG. 22 shows a histogram of the intensity $I_0$ of forward scattered light produced by the histogram generate means. In this graph, the portion of the histogram below the minimal point p represents a portion corresponding to a noise due to the ghost and/or dust described above.

In consequence, when the minimal point p is detected by the minimal point detect means, the unnecessary information remove means sets the noise threshold as shown in FIG. 3b by use of the minimal point p so as to remove the noise. That is, the cell analyzer in accordance with the present invention operates to remove the noise by means of the software, and hence it is possible to automatically set the optimal threshold for each sample.

As described above, according to the present invention, the optimal noise threshold can be automatically established for each sample and hence the efficiency and reliability of the cell analysis are advantageously increased.

In addition, according to the present invention, there is provided an apparatus including sample supply means for sequentially sipping a plurality of samples so as to supply the sipped samples to the flow cell and measurement condition set means for setting to the cell light information process means an optimal measurement condition associated with each said sample supplied from the sample supply means.

In the cell analyze device according to the present invention, the sample supply means sequentially passes samples to the flow cell so as to effect measurements in a sequential fashion such that even for a different processing method of a sample, the measurement condition set means automatically sets the measurement condition associated therewith. In consequence, it is possible to conduct measurements of a great number of samples with highly efficiency while improving the reliability of the measurement results.

BRIEF DESCRIPTION OF THE DRAWINGS

These and other objects and advantages of the present invention will become apparent by reference to the following description and accompanying drawings wherein:

FIGS. 4 to 9 are schematic diagrams showing a first embodiment according to the present invention.

FIG. 4 is a block diagram useful to explain the constitution of the cell analyze apparatus of the first embodiment;

FIG. 5 is a flowchart showing the operation of the cell analyze apparatus;

FIG. 9 is a schematic cytogram useful to explain the parameter conversion;

FIG. 10 is a schematic diagram for explaining the constitution of the cell analyzer of the second embodiment;

FIG. 11 is a flowchart showing the operation of the cell analyzer of FIG. 10;

FIGS. 12 to 15c are diagrams showing a third embodiment according to the present invention.

FIG. 12 is a flowchart showing the operation of the overall cell analyzer of FIG. 10;

FIG. 13 is a flowchart showing the operation of the final subdivide operation of the cell analyzer;

FIG. 14 is a diagram showing the primary portion of the cytogram represented with contour lines for explaining the final subdivide operation of the cell analyzer;

FIGS. 15a, 15b, and 15c are schematic histograms useful to explain the final subdivide operation of the cell analyzer;

FIGS. 16 to 18b are diagrams showing a fourth embodiment according to the present invention.

FIG. 16 is a flowchart showing the operation of the cell analyzer of the fourth embodiment;

FIG. 17 is a diagram showing the primary portion of the cytogram represented in three dimensions for explaining the final fraction determination of the cell analyzer;

FIGS. 18a and 18b are schematic histograms useful to explain the final fraction determination of the cell analyzer;

FIGS. 19 to 22 are diagrams showing a fifth embodiment according to the present invention;

FIG. 19 is a schematic diagram showing the constitution of the cell analyzer of the fifth embodiment;

FIG. 20 is a block diagram showing the constitution of the signal process circuit of the cell analyzer;

FIG. 21 is a flowchart useful to explain the operation of the cell analyzer; and FIG. 22 is a schematic histogram representing the intensity of forward scattered light in the cell analyzer.

DESCRIPTION OF THE PREFERRED EMBODIMENTS

Figure 1:
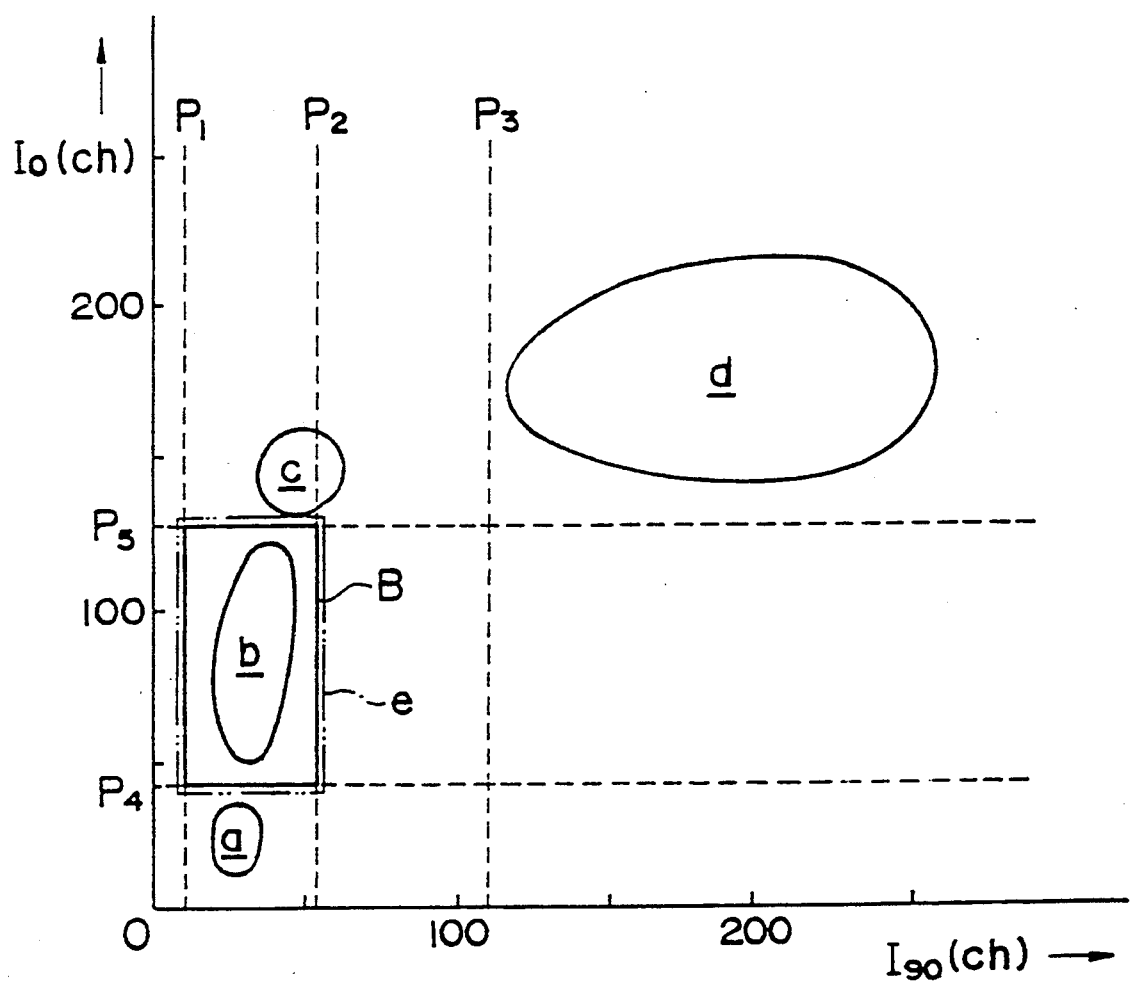
FIG. 1 is a schematic diagram showing an example of a cytogram of the intensity of forward scattered light and right angle scattered light.

Description will now be given in detail of the first embodiment according to the present invention. In this embodiment, a minimal point is to be detected through a coordinate conversion effected on a histogram.

The cell analyze apparatus of this embodiment adopts as cell light information (to be simply called data in some cases) all of four parameters including the intensity of forward scattered light $I_0$, the intensity of right angle scattered light $I_{90}$, and intensities Ir and Ig of fluorescence of two different colors, respectively.

FIG. 4 is a block diagram showing the configuration of the cell analyzer including a flow cell formed with quartz or the like such that a sample (cell float liquid) including cells conjugated with fluorescent dye flows together with sheath fluid through an inside space (flow channel) 10a of the cell 10. In the flow channel 10a, there is formed sheath flow such that the cells of the sample flow in a line along the center axis of the flow channel in a cell-by-cell fashion due to the hydrodynamic focusing effect.

The sample and sheath fluid are supplied to the flow cell 10 in an automatic manner by means of a fluid supply or feed device 13, which includes a plurality of injector cylinders and a sample supply section and is controlled by a microcomputer (MPU) 21, which will be described later.

The configuration also comprises an argon laser unit 14 as a light source, which irradiates a laser beam with a wavelength of 488 nanometers (nm) onto each cell flowing through the flow channel 10 along the center axis thereof. Incidentally, the light source is not restricted by the argon laser, namely, a helium-neon laser, a helium-cadmium laser, various dye lasers and so on can also be employed.

In the periphery of the flow cell 10, there are arranged lenses 16a, 16b, a beam blocker 17, and dichroic mirrors 18a, 18b. A forward scattered light emitted from the cell 1 is converged through the lens 16a and is then fed to a photodiode (cell light information detect means) 15a. Incidentally, the beam blocker 17 is disposed to prevent the laser beam from directly entering the photodiode 15a.

A right angle scattered light passes through the lens 16b so as to be reflected by the dichroic mirror 18a and is then supplied to a photoelectric multiplier (cell light information detect means) 15b. A portion of the fluorescence radiated from the cell travels through the lens 16b and the dichroic mirror 18a and is then reflected on the dichromatic mirror 18b so as to be delivered through a green filter 19c to a photoelectric multiplier (cell light information detect means) 15b for detecting a green fluorescence. Another portion of the fluorescence radiated from the cell passes through the lens 16b and the dichroic mirrors 18a and 18b so as to be fed via a red filter 19d to a photoelectric multiplier (cell light information detect means) 15d for detecting a red fluorescence.

The photodiode 15a and the photoelectric multiplier tubes 15b, 15c, and 15d produce outputs, which are fed via an amplifier and an analog-to-digital converter, not shown, to the MPU 21.

The MPU 21 includes functions such as a function to convert the intensity of scattered light and $I_{90}$ in a manner which will be described later, a function to create histograms with respect to the intensity of scattered light $I_0$ and $I_{90}$ and the converted results $I_0'$ and $I_{90}'$ of the intensity of scattered light, a function to detect minimal points in these histograms so as to subdivide a cell population, a function to collect (extract) cell light information of an objective cell population, and a function for achieving an analyze processing on fluorescent characteristics of the objective cell population based on the collected cell light information.

To the MPU 21, there is connected a keyboard 22, which is employed to input information items including a protocol such as a measurement condition, attributes of a patient, and an instruction.

Referring next to FIG. 5 associated with an example of an analysis of lymphocyte subset in blood, description will be given of the operation of the cell analyze apparatus of this embodiment.

First of all, there is prepared a sample for the cell analysis such that blood obtained from the patient is subjected to hemolysis as described above so as to remove red blood cell after two kinds of monoclonal antibodies respectively conjugated with the different fluorescent dye are caused to react upon the blood, thereby producing the sample. For example, as described above, the monoclonal antibodies include an OKT4 monoclonal antibody conjugated with fluorescein isothiocyanate (FITC; green fluorescence) and an OKT8 monoclonal antibody conjugated with phycoerythrin (PE; red fluorescence).

The sample thus prepared is installed in the sample fluid supplier or feeder 13. In this situation, if the measurement start instruction is inputted from the keyboard 22 together with the protocol and attribute data of the patient, the system initiates the measurement (step 1 or ST1).

The sample is then delivered from the sample feeder 13 to the flow cell 10 such that the laser beam is irradiated onto cells contained in the sample so as to detect the intensity of forward scattered light $I_0$, the intensity of right angle scattered light $I_{90}$, the green fluorescence intensity $I_g$, and the red fluorescence intensity $I_r$ (ST2).

For each cell of the sample, the measured values of $I_0$, $I_{90}$, $I_g$, and $I_r$ are stored in a memory of the MPU 21 in a form of a so-called list format. Incidentally, the list format requires a large capacity of the memory and hence the memory cost is soared; in consequence, an external storage is employed for a low-cost cell analyzer.

Subsequently, the system generates histograms associated with the intensity of forward scattered light $I_0$ and the intensity of right angle scattered light $I_{90}$ (ST3), and then it is judged to determine whether or not a minimal point can be detected from the histogram for each intensity (ST4).

Figure 2A:
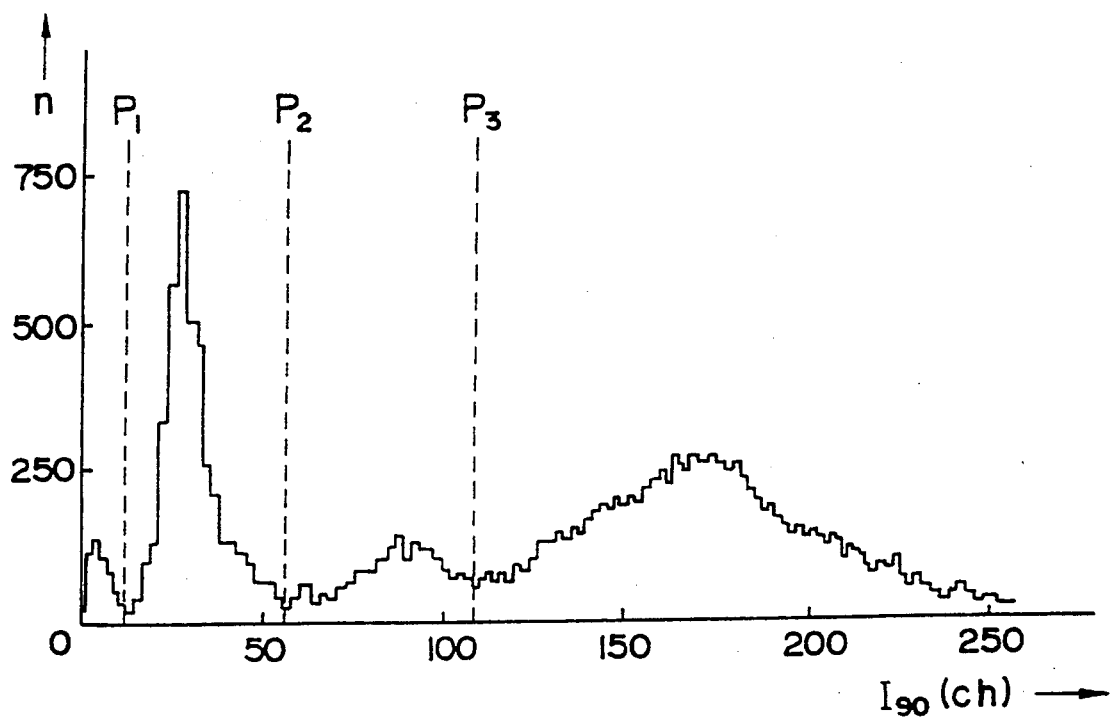
FIGS. 2a and 2b are graphs showing examples of histograms associated with the intensity of forward scattered light and right angle scattered light, respectively.
Figure 2B:
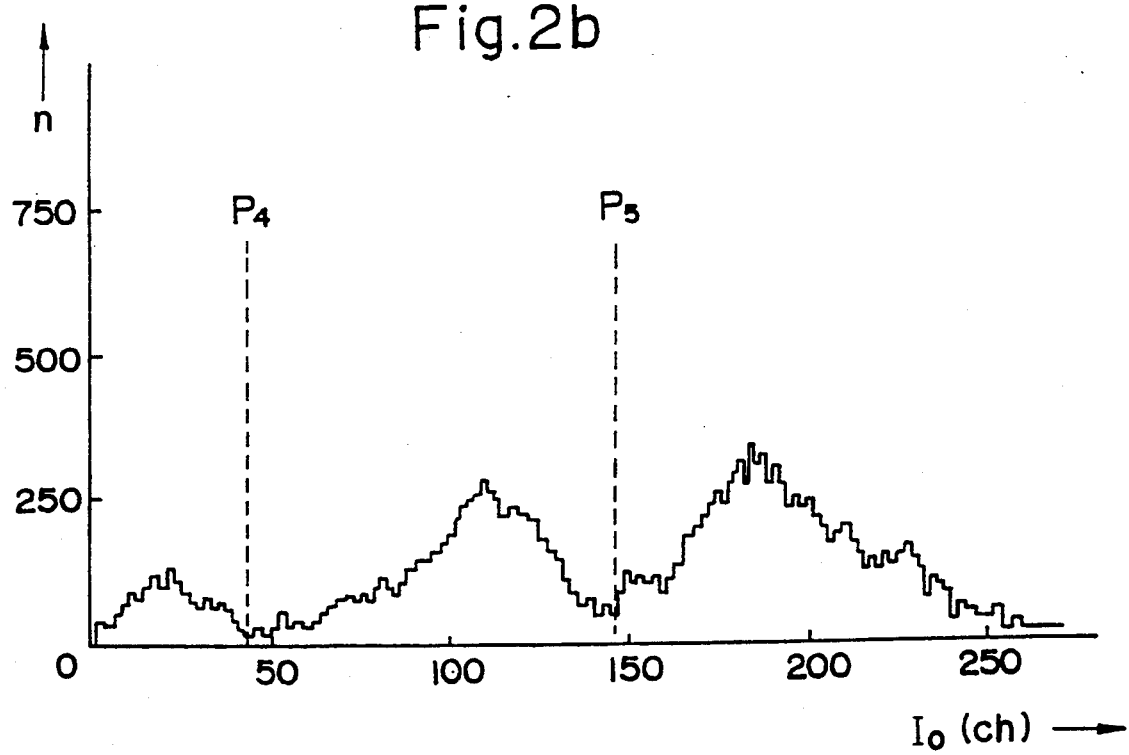

For a normal subject, there are attained the histograms of $I_{90}$ and $I_0$ as shown in FIGS. 2a and 2b, respectively. In this case, the histogram of $I_{90}$ includes four peaks and three troughs (minimal points); whereas the histogram of $I_0$ includes three peaks and two troughs (minimal points). Consequently, the system can detect minimal points $p_1$, $p_2$, and $p_3$ from the histogram of $I_{90}$ and minimal points $p_4$ and $p_5$ from the histogram of $I_0$. That is, the judgement in ST4 results in YES, and hence the processing proceeds to ST5.

In ST5, the first minimal points $p_1$, $p_2$, and $p_3$ are detected from the histogram of $I_{90}$. Since the fraction related to the lymphocytes belongs to a region between the minimal points $p_1$ and $p_2$, the system separates and extracts data for which $I_{90}$ is at least $p_1$ and at most $p_2$, thereby generating a histogram of $I_{90}$ for the separated data as shown in FIG. 6a.

Figure 6A:
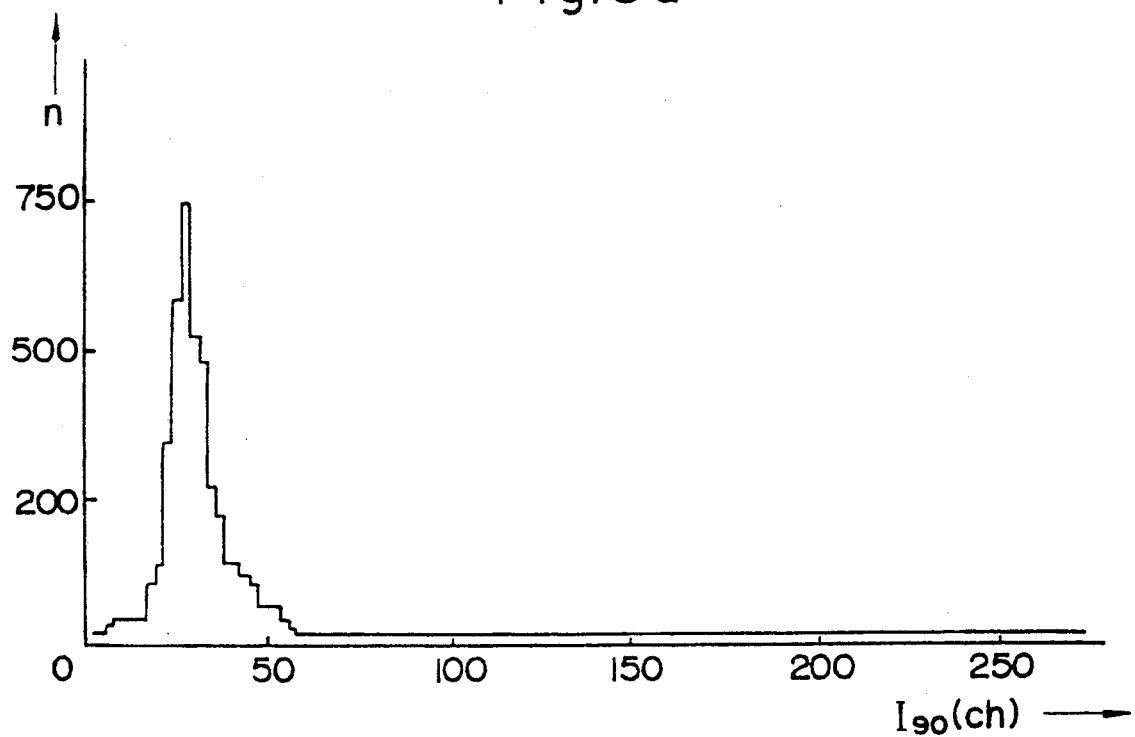
FIGS. 6a and 6b are histograms of the intensity respectively of forward scattered light and right angle scattered light useful to explain the fraction extract operation of the cell analyze apparatus.

Subsequently, the system creates a histogram of $I_0$ for the separated data as shown in FIG. 6a so as to extract minimal points by use of the histogram (ST7). Thereafter, based on the extracted minimal points, a fraction of the lymphocytes is finally determined (ST8). The minimal points associated with $I_0$ can also be extracted from the histogram of FIG. 2b as described above.

Figure 6B:
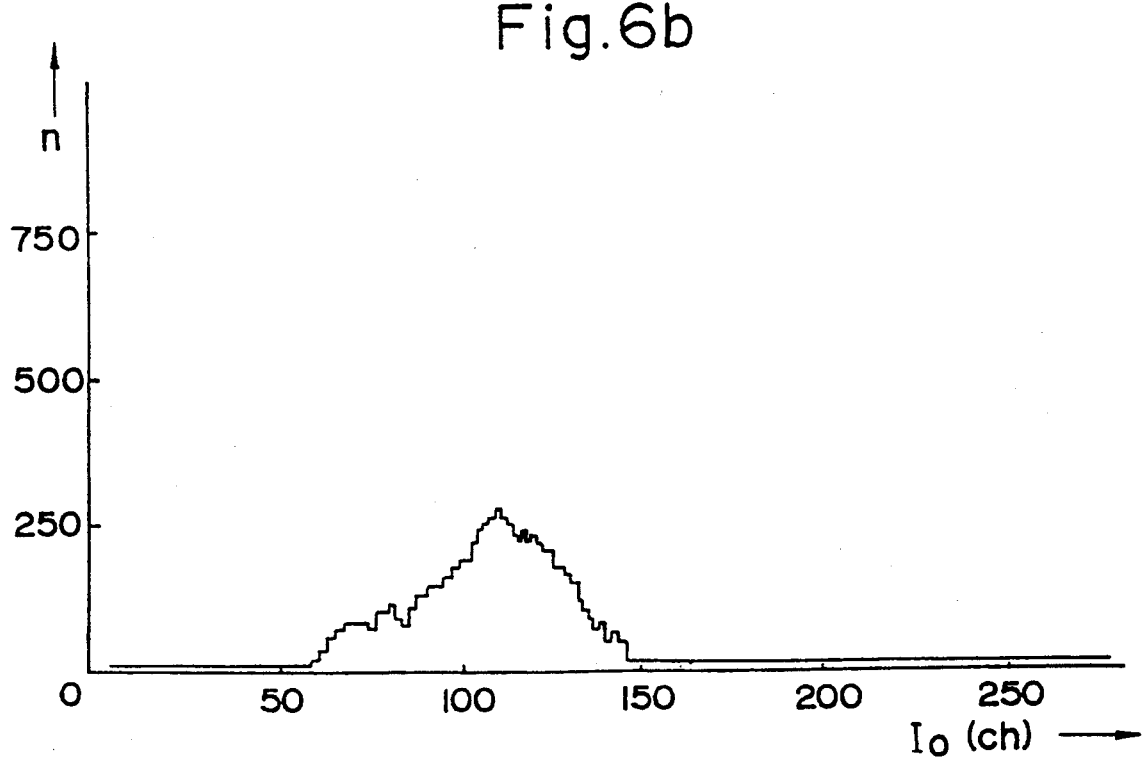
Figure 7A:
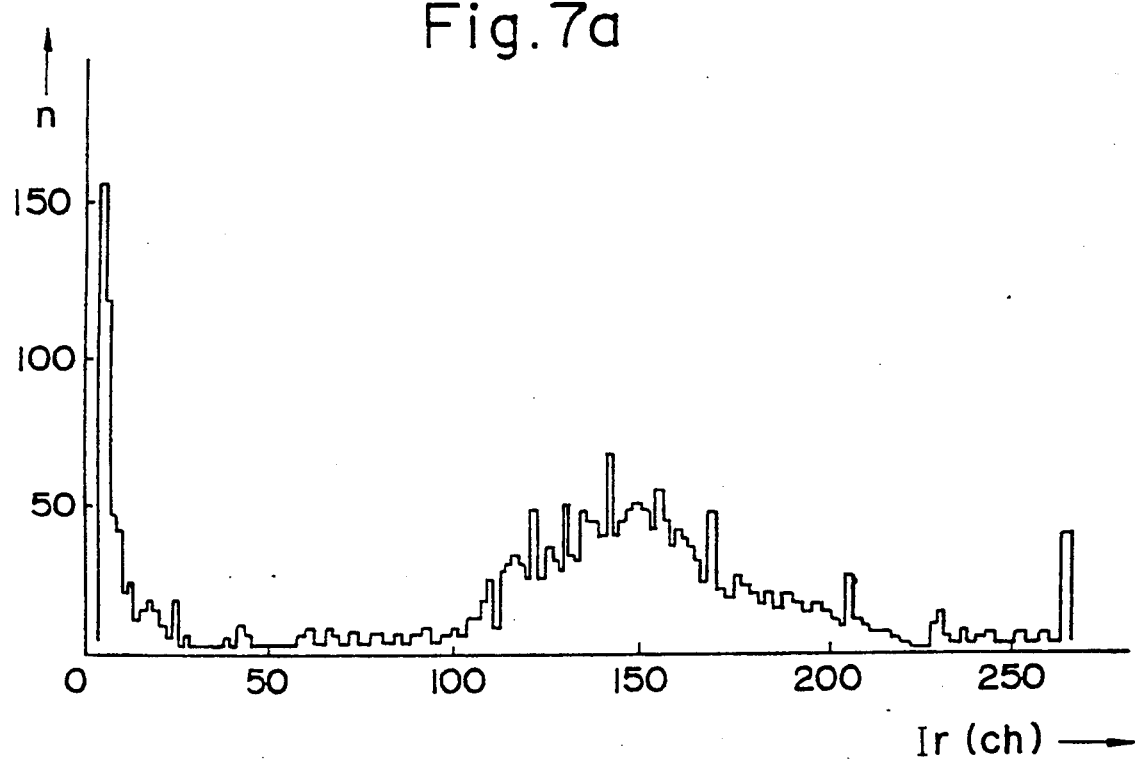
FIGS. 7a and 7b are graphs showing examples of the histogram associated with the red and green fluorescence intensity with respect to data items respectively collected.
Figure 7B:
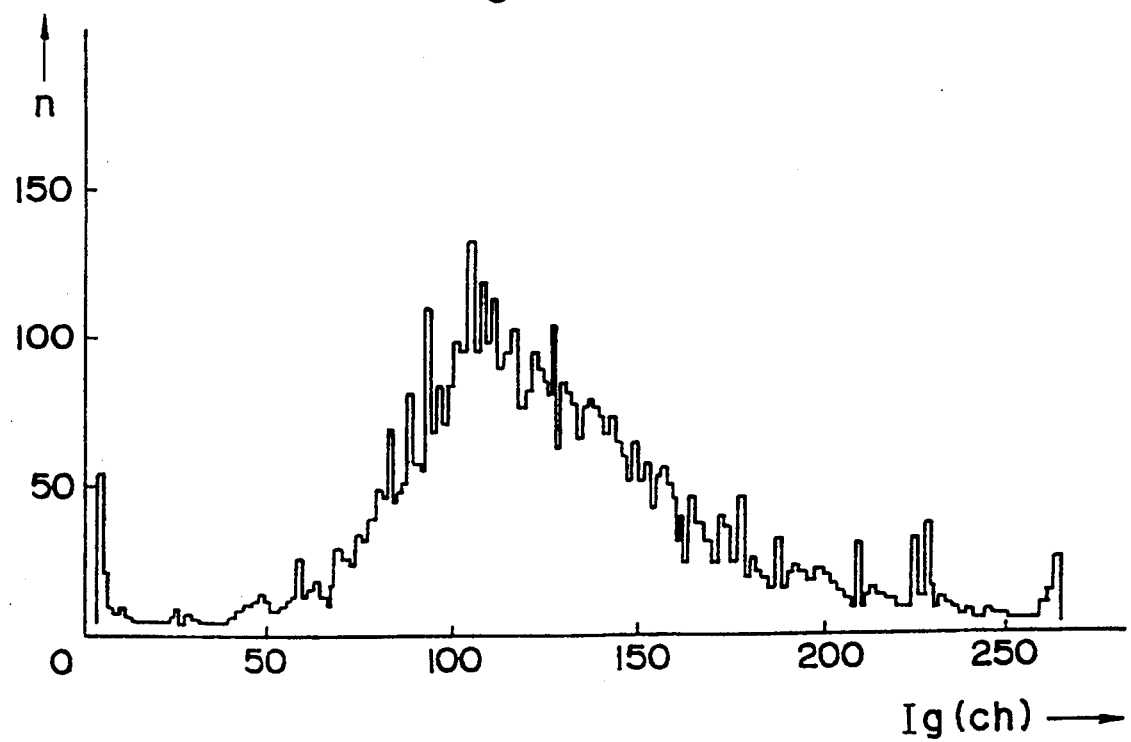

The MPU 21 further separates and extracts from the data thus obtained in ST6 data between the minimal points $p_4$ and $p_5$ determined in ST7 as shown in FIG. 6b so as to collect data belonging to the fraction B of lymphocytes, thereby conducting an analyze processing on the red fluorescence intensity $I_r$ and the green fluorescence intensity $I_g$ in the data thus collected (ST9). In this analysis, histograms are produced for $I_r$ and $I_g$ as shown in FIGS. 7a and 7b, or cytograms are generated for $I_r$ and $I_g$. These histograms and cytograms (including those associated with $I_0$ and $I_{90}$) are displayed on the CRT 23 when necessary (ST10).

In ST11, a check is effected to determine whether or not a print instruct ion has been inputted to the system. If the judgement results in NO, control is directly passed to ST13; whereas, the processing proceeds to ST12 if the result is YES so as to print out the analysis results on a sheet of paper by means of the printer 24.

In ST13, judgement is conducted to determine whether or not a measurement end instruction has been received. If the judgement results in NO, namely, if the sample measurement is to be continued, the processing returns to ST1; whereas, if the result is YES, the measurement is terminated.

Figure 8A:
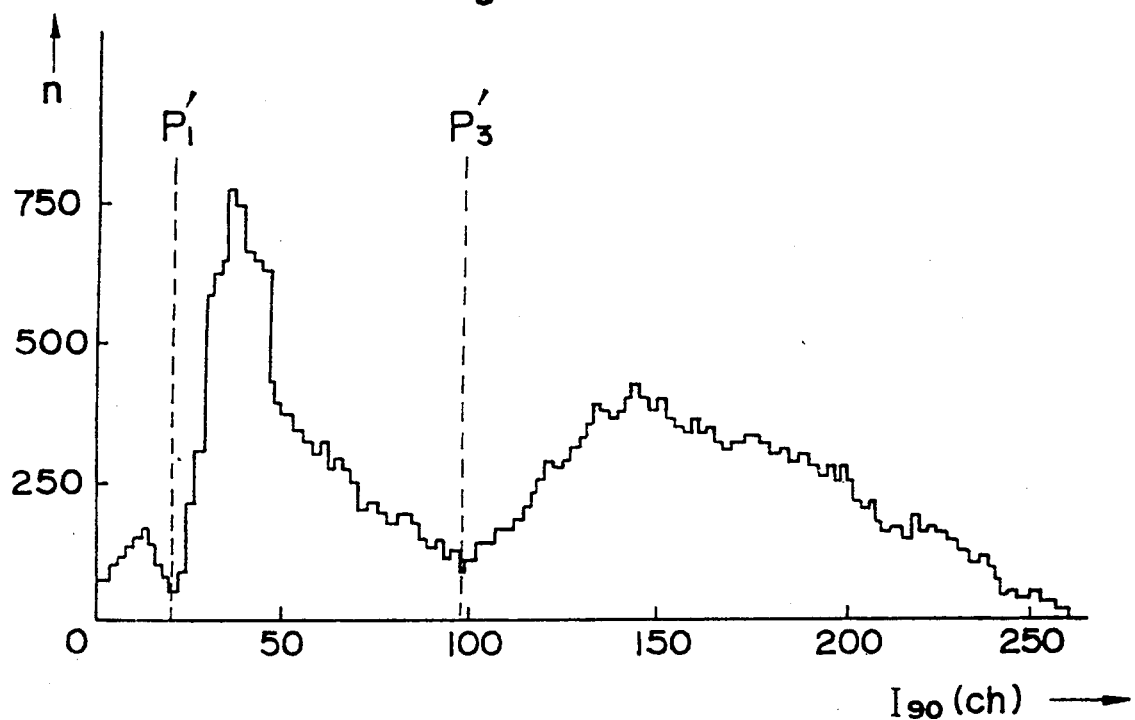
FIGS. 8a and 8b are histograms for explaining cases where minimal points cannot be detected for the intensity of right angle scattered light.
Figure 8B:
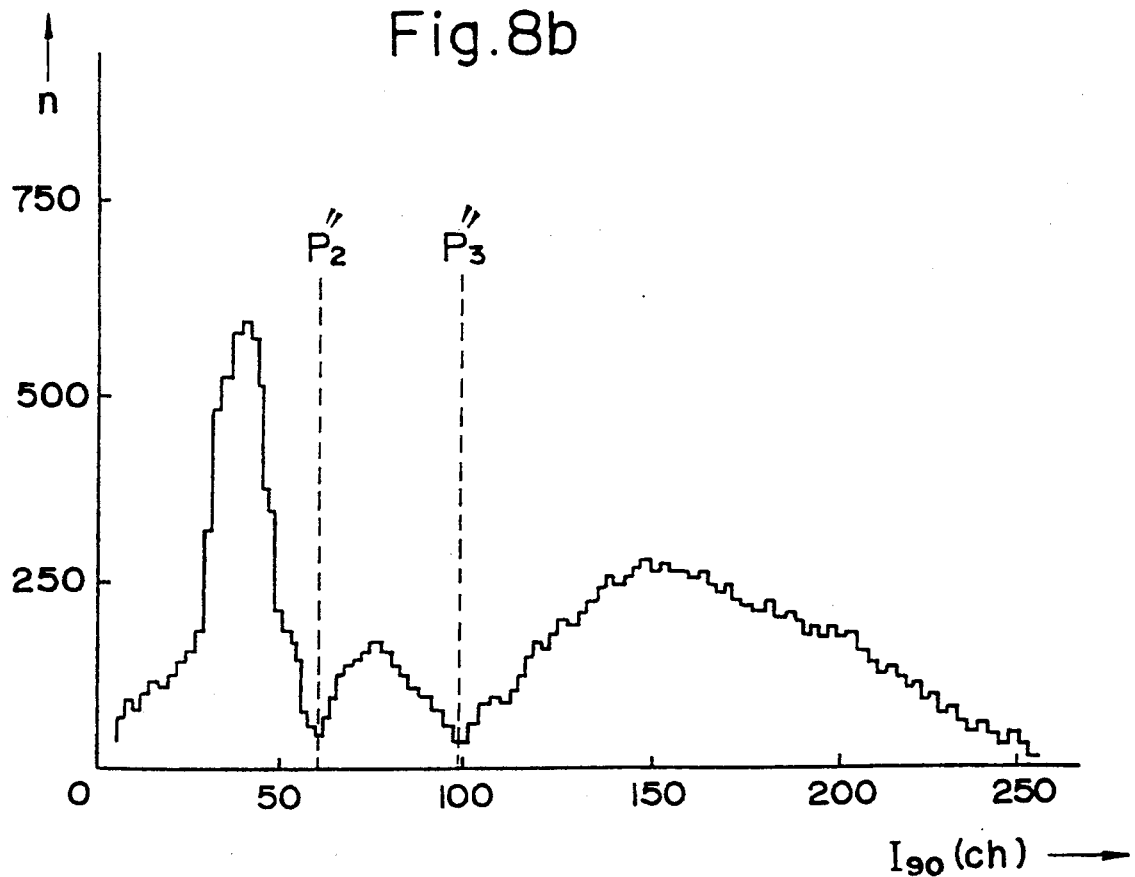

In some case, however, such minimal points cannot be necessarily extracted from the histograms of $I_{90}$ and $I_0$ produced in ST3. For example, as for $I_{90}$, the minimal point $p_2$ or $p_1$ is not detectable as shown in FIG. 8a or 8b, respectively. It is natural that the judgement in ST4 results in NO in this case.

When NO results in ST4, control is transferred to the processing of ST14 so as to convert all the measured data associated with $I_{90}$ and $I_0$ into new parameters and $I_{90}'$ and $I_0'$ based on the following conversion expressions (1) and (2).

$$I_0' = \alpha_1 \cdot (I_0 + \beta_1 \cdot I_{90}) + \gamma_1 \tag{1}$$

$$I_{90}' = \alpha_2 \cdot (I_{90} + \beta_2 \cdot I_0) + \gamma_2 \tag{2}$$

Figure 9:
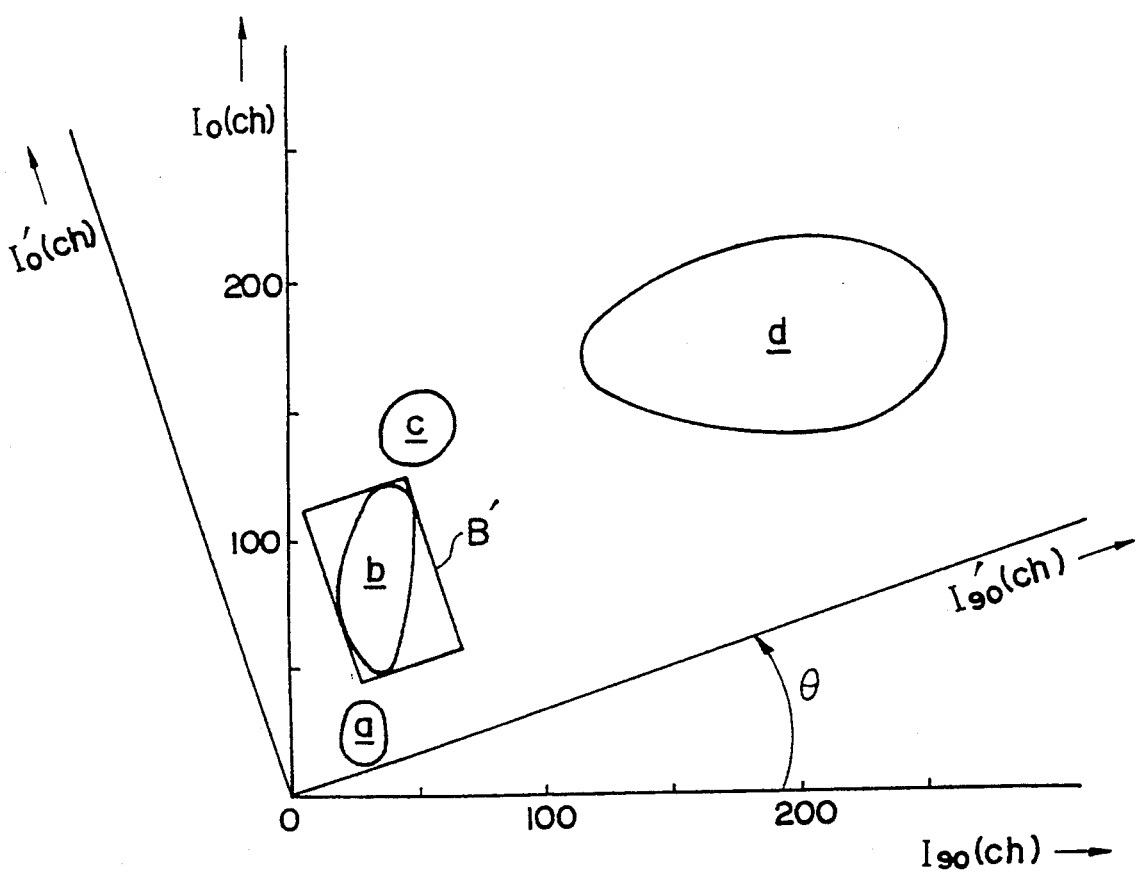

In the expressions (1) and (2), the constants $\alpha_1$, $\beta_1$, $\gamma_1$, $\alpha_2$, $\beta_2$, and $\gamma_2$ are optimized so that the minimal points are detected from the converted $I_{90}'$ and $I_0'$ so as to determine a fraction of lymphocytes: For example, FIG. 9 shows an example of data conversion in which the coordinate system related to $I_{90}$ and $I_0$ is rotated by $\theta$. Naturally, the simple rotation does not restrict the conversion, namely, any modifications may be appropriately carried out for the conversion.

In ST15, histograms are produced for the converted $I_{90}'$ and $I_0'$. Thereafter, ST 16 checks to determine whether or not minimal points are detectable in the generated historgrams. If the judgement results in YES, control returns to ST5 so as to execute the processing in the similar fashion to determine the fraction B' of lymphocytes (refer to FIG. 9 for details). On the other hand, for a patient having various kinds of states of a disease, the minimal point cannot be extracted even after the conversion of the histograms, which hence causes the judgement to results in NO in some cases. In this situation, the data is stored in the memory and an alarm display is effected on the CRT 23 so as to sound an alarm tone, which notifies the minimal point undetectable state to the operator, thereby interrupting the processing. Incidentally, the system may also be appropriately modified, for example, when the check of ST16 results in NO, another conversion may be carried out.

In addition, the description has been given of an example of the analysis of lymphocyte subset; however, the present invention is not restricted by this example, namely, the present invention is broadly applicable to analyses of populations of various cells such as erythrocytes, reticulocytes, and thrombocytes. In consequence, the parameters associated with the conversion are not limited to the intensity of forward scattered light $I_0$ nor to the intensity of right angle scattered light $I_{90}$. Furthermore, the system may be configured so as to cooperate with an auto-sampler.

Next, description will be given of a second embodiment of a configuration in which there is developed a cooperative operation between the system and an auto-sampler.

Figure 10:
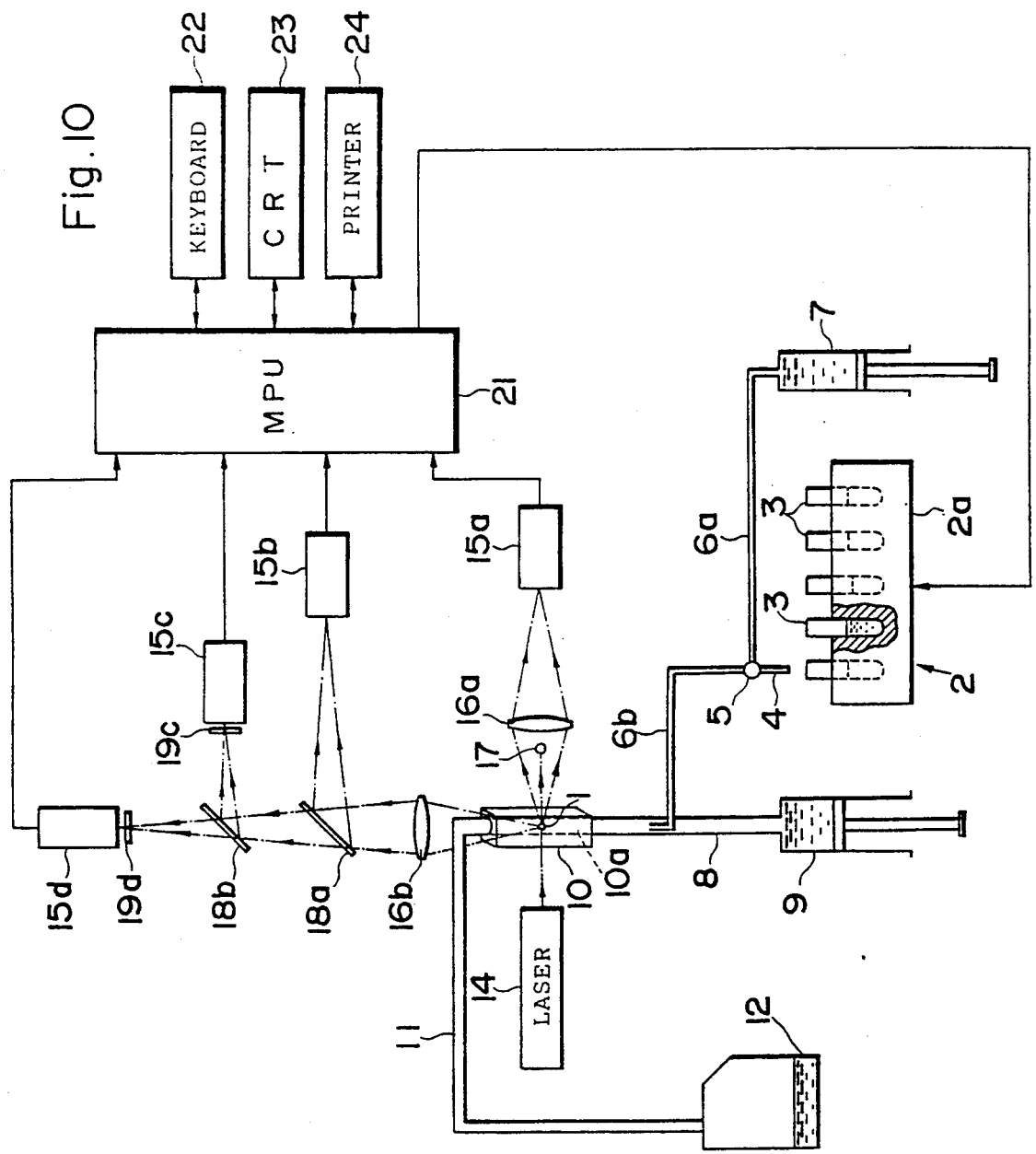
FIGS. 10 and 11 are diagrams showing a second embodiment according to the present invention.

FIG. 10 shows a cell analyze apparatus of the second embodiment according to the present invention in which the constituent elements identical to those shown in FIG. 4 are assigned with the same reference numerals.

This constitution includes an auto-sampler 2 having a sample rack 2a (only one rack unit is shown here) disposed to install therein a plurality of sample containers 3. The sample rack 2a is driven by means of drive mechanism, not shown, so as to locate a specified sample at a position directly below a sample sip tube 4. In addition, the sample rack 2a is provided with shaking mechanism and cooling mechanism, not shown, such that the sample is subjected to shaking operation at a predetermined interval of time and that the samples of the sample container 3 mounted in the system are kept remained at a low temperature (for example, at temperatures ranging from 4° C. to 10° C.).

For example, samples are set to the auto-sampler 2 as follows. Blood obtained from a patient is processed in five different processing methods α, β, γ, δ, and ε such that the resultant samples are contained in the respective five sample containers 3, which are then installed in the auto-sampler 2. That is, for a patient, five kinds of samples are set to the auto-sampler 2; consequently, the number of samples to be processed is obtained by multiplying the number of patients by five.

On the other hand, the sample sip tube 4 is connected to a port of a three-directional valve 5 of which two other ports are linked to sample feed tubes 6a and 6b, respectively such that a communication may be established between the sample feed tube 6a and the sample sip tube 4 or between the sample feed tubes 6a and 6b. The sample feed tube 6a has another end at which the sample pump 7 is disposed; whereas the sample feed tube 6b possesses another end which opens into an inside of a sheath supply tube 8.

The sheath fluid supply tube 8 has an end connected to a sheath pump 9 and other end linked to a flow cell 10 constituted with a material such as a quartz glass through which a light having a wavelength employed for the measurement passes. The flow cell 10 includes a flow channel 10a therein such that sheath flow is formed in the flow channel 10a, namely, as described above, owing to the hydro-dynamic focusing effect, the cells or particles of the sample flow in a line through the flow channel 10a along the center axis thereof.

The fluid flown out from the flow cell 10 is guided by a discharge tube 11 into a discharge tank or container 12. The cell analyzer includes a sheath fluid tank or container, not shown, such that the sheath fluid is supplied to the sample pump 7 and the sheath pump 9. In addition, the components such as the auto-sampler and the pumps 7 and 9 constitute a fluid feed system, which can be hermetically sealed and hence a bio-hazard can be prevented.

In the periphery of the flow cell 10, there are disposed a laser (light source) 14 and photosensors or light detectors (cell light information detect means) 15a, 15c, 15c, and 15d. The laser 14 irradiates a laser beam onto a cell (or a particle) I flowing through the flow channel 10a. The cell thus irradiated by the beam emits light in the forward direction which is converged as a forward scattered light by means of a lens 16a so as to be fed to the photosensor 15a. The configuration also includes a beam blocker 17 which prevents the laser beam from directly entering the photosensor 15a.

On the other hand, light emitted in a direction of a right angle from the cell (or the particle) 1 is focused by a lens 16b such that a portion of this light is reflected on a dichroic mirror 18a so as to be fed to the photosensor 15b for detecting a right angle scattered light. A portion of the light which has traveled through the dichroic mirror 18a is then reflected on another dichromatic mirror 18b so as to be transferred through a filter 19a to the photosensor 15c for detecting a green fluorescence. The light which has passed through the dichromatic mirror 18b is sent via a filter 19b to the photosensor 15d for detecting red fluorescence. For example, an argon or a helium laser is used as the laser 14; a photodiode is adopted as the light detector 15a for detecting a forward scattered light; and photoelectric multiplier tubes are employed for the photosensors 15b to 15d.

The photosensors 15a to 15d deliver the received signals to an analog-to-digital converter, not shown, such that the digital signals thus converted are supplied to an MPU 21. The MPU 21 has various functions such as a function to generate, based on the received signals, cytograms and histograms related to the forward scattered light intensity $I_0$ and the intensity of right angle scattered light $I_{90}$, a function to discriminate data of objective cell (particle) populations, land a function to analyze, based on the discriminated data, the green fluorescence intensity Ig and the red fluorescence intensity Ir so as to determine positive ratios associated with the green and red fluorescence, and a function to control the auto-sampler 2, the sample pump 7, and the sheath pump 9.

To the MPU 21, there are connected a keyboard 22, a cathode-ray tube (CRT) 23, and a printer 24. The keyboard 22 is adopted to supply the MPU 21 with an instruction for a mode specification, an instruction to select and to set a protocol (measurement condition), and other instructions. The CRT 23 is used to monitor a state of measurement; whereas the printer (output means) 24 is employed to print out on a sheet of paper results of processing such as a cytogram and a histogram.

Next, referring to FIG. 11, description will be given the operation of the cell analyze equipment of this embodiment.

When the power system of the cell analyze equipment is turned on, the MPU 21 is loaded with a program read from a read-only memory (ROM), not shown, and then the system initiates an operation so as to first effect a mode selection (ST21).

The system operates in three modes including an automatic mode, a semi-automatic mode, and a manual mode. Description will now be given of the operation on assumption that the automatic mode is selected. In the automatic mode, the samples installed in the autosampler 2 are automatically and sequentially measured in a specified order. The samples are specified as, for example, a sample $(5-\alpha)$ obtained by processing an objective fluid of the fifth patient by use of a processing method $\alpha$, a sample $(3-\gamma)$ obtained by processing an objective fluid of the third patient by use of a processing method $\gamma$, and so forth. It is to be understood that the same sample may be specified for two measurements.

In the subsequent step ST22, a protocol is selected and is established for a sample to be measured. The protocol is constituted with specification items such as a detection gain and a content of a correction for each of the photosensor 15a to 15d. For the protocol setting and establishing operation, there are beforehand supplied optimal numeric values for the samples to which the processing methods $\alpha$ to $\epsilon$ are applied such that the specifications of the protocol contents are automatically changed over so as to select an optimal protocol in a sequence of the measurements. For example, in a case where the samples are specified as $(5-\alpha)$, $(3-\gamma)$, and so forth, the system effects a change-over operation of the protocols so as to sequentially select a protocol for the processing method $\alpha$, a protocol for the processing method $\gamma$, and so forth.

The selection and setting of the protocol may be achieved by another opertion, in addition to the operation above, to set the system to a protocol input wait state when a measurement of a specified sample is finished so as to specify another protocol or an operation to input a protocol for each sample. Alternatively, an external computer or the like may be used to select and to set a protocol.

Incidentally, the semi-automatic mode is used to conduct a measurement only for a specified sample; for example, if the operator specifies $(4-\beta)$, the system selects from the samples of the fourth patient a sample processed by use of the processing method $\beta$ such that the selected sample is sucked and that a protocol associated with the processing method $\beta$ is automatically selected for the measurement. On the other hand, in the manual mode, there is conducted a measurement only for a specified sample; however, this mode is different from the semi-automatic mode in that the protocol is supplied in a manual fashion.

When ST22 is completed, the sample rack 2a is driven so as to locate the sample container 3 in which a sample to be first subjected to measurement is contained to a position directly beneath the sample sip tube 4. Thereafter, the three-directional valve 5 is set to communicate the sample sip tube 4 with the sample supply tube 6a and that the sample pump 7 is driven for the sip operation side, thereby sipping the sample into the sample feed tube 6a (ST23).

Next, the three-directional valve 5 is changed-over to a state for communicating the sample feed tubes 6a with the sample feed tubes 6b and the sample pump 7 is driven for the fluid feed side, which causes the sample to be delivered to the sheath supply tube 8. On the other hand, the sheath pump 9 is driven for the fluid feed side and hence the sheath is fed to the flow cell 10. In the flow channel 10a, there is formed a sheath flow such that due to the hydro-dynamic focusing effect, the cells of the supplied sample flow in a line through the flow channel 10a along a center axis thereof. The laser beam is irradiated onto each of these cells so as to respectively measure the forward scattered light intensity $I_0$, the intensity of right angle scatteredlight $I_{90}$, the green fluorescence intensity $I_g$, and the red fluorescence intensity $I_r$ (ST24).

The data thus measured is processed in a predetermined procedure. For example, in an analysis of leucocytes, the system produces a cytogram associated with the forward scattered light intensity $I_0$ and the right angle scattered light intensity $I_{90}$ (refer to FIG. 1 for details). In the cytogram, there are drawn a distribution $\underline{b}$ of lymphocytes, a distribution $\underline{c}$ of monocytes and a distribution $\underline{d}$ of granulocytes. In this case, a distribution $\underline{a}$ of particles such as membrane components of red blood cell called debris is removed at a stage of the noise processing in many cases.

In ST25, for the distributions $\underline{b}$, $\underline{c}$, and $\underline{d}$ respectively of the lymphocytes, monocytes, and granulocytes, the system respectively sets, for example, the analysis regions (partitions or fractions) so as to compute necessary information items such as average intensity, standard deviation (SD), and coefficient of variation (CV) so as to compare these computed values with the respective reference values beforehand stored in the system, thereby judging the normality or abnormality of each of the data. If the judgement results in NO, namely, if the data are normal, there are effected a computation of the data so as to attain the positive ratios and other items, and then control is transferred to ST26.

On the other hand, if the judgement of ST25 results in YES, namely, the data are abnormal, control is passed to ST30 in which the data are stored in list memory, not shown, of the MPU 21 (ST30) and then a check is conducted to determine whether or not the analysis fraction is rearranged (ST31). If YES is attained as a result of the judgement of ST 31, the processing branches to ST32 so as to rearrange the analysis partition and to compute the operation again based on the rearranged partition, and thereafter control is transferred to ST26. It is natural that the conversion processing may also be carried out in this situation like in the case of the first embodiment described above. If the judgement of ST31 results in NO, cotrol is directly passed to ST26.

In ST26, the results of the computation are displayed on the CRT 23 and are printed out on a sheet of paper by means of the printer 24. In the subsequent ST27, a check is made to determine whether or not there remains any sample to be measured such that if this check results in YES, the processing branches to ST22 to effect a change-over operation to set a protocol associated with the next sample for the measurement. If the judgement of ST27 results in NO, the system judges to determine whether or not the measurement is to be finished (ST28). If YES is attained as a result of this judgement, the measurement is terminated; whereas if NO is resulted, control is passed to ST29 in which the next sample is set and then the processing branches again to ST21 so as to start the measurement again.

Incidentally, the description has been given of a case where the samples are measured in an automatic manner (automatic mode); however, the system also allows an interrupt measurement, for example. In a case where the interrupt measurement is desired, when a sample beforehand installed is removed, there is established a state in which the sample is missing such that a sample is set for the interrupt measurement through ST27, ST28, and ST29 and that the mode is changed over so as to conduct the measurement.

The parameters employed in the measurements are not limited to the four parameters above including the forward scattered light intensity, the intensity of right angle scattered light, the green fluorescence intensity, and the red fluorescence intensity, namely, other arbitrary parameters may be used depending on the system design.

According to the third embodiment, the cell analyze apparatus is further improved, and the constitution of FIG. 4 or 10 may be applicable to this embodiment. Description will be given of a case where the configuration of FIG. 10 is employed in the third embodiment.

Figure 12:
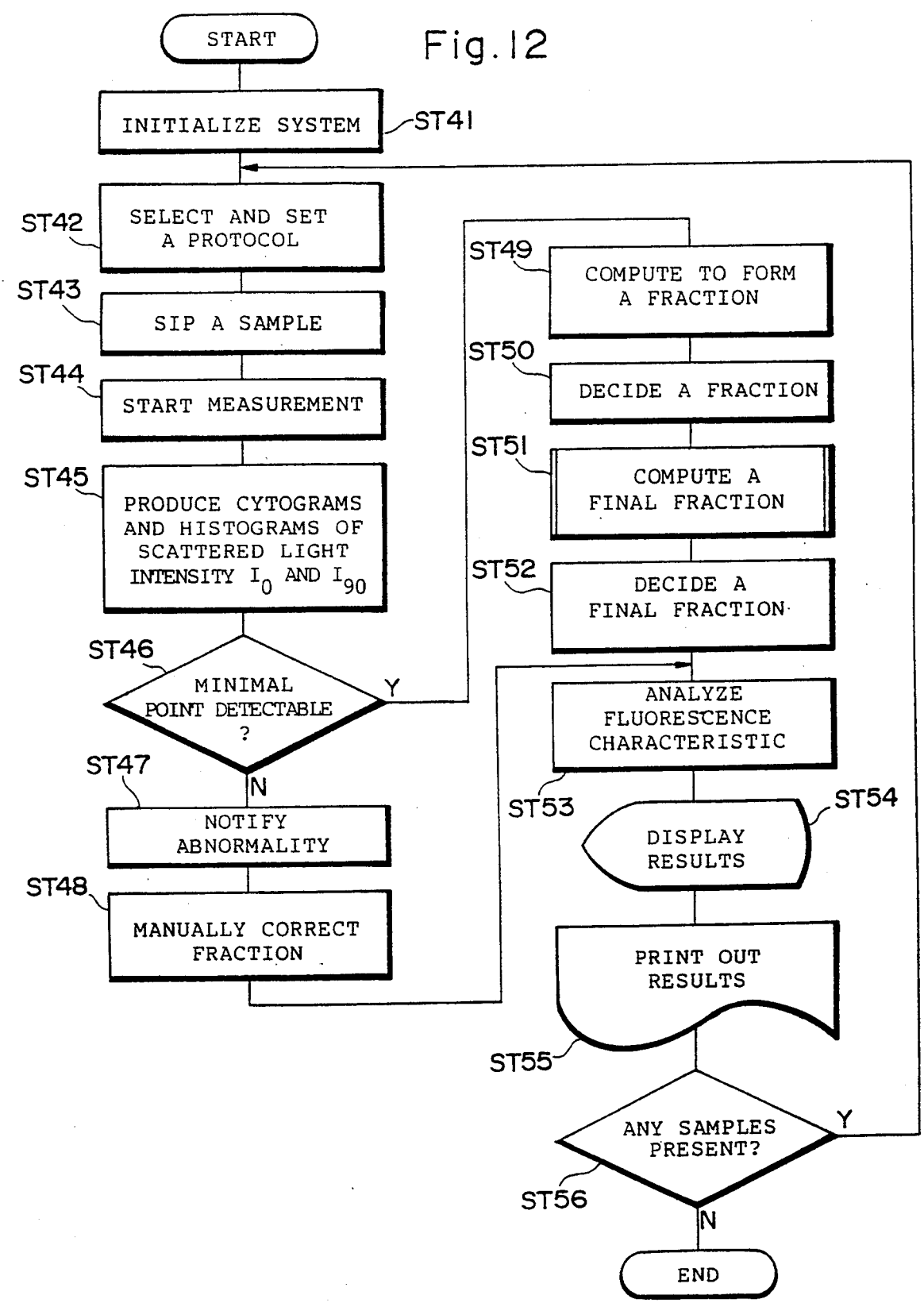

The MPU 21 has various functions such as a function to produce cytograms and histograms associated with the forward scattered light intensity $I_0$ and right angle scattered light intensity $I_{90}$, a function to extract minimal points from the histograms thus produced and to subdivide cell light information into fractions, a function to collect cell light information of each of the the fractions, a function to determine the final fraction for the collected cell light information, a function to collect the cell light information belonging to the final fraction so as to analyze the fluorescence characteristics, and a function to control the sample pump 7, the sheath pump 9, and the auto-sampler 2. Referring next to FIG. 12, description will be given of the operation of the cell analyze equipment according to the third embodiment.

First, samples undergone pertinent processing associated with analysis purposes are installed in the respective sample cases or containers 3 so as to be mounted on the sample rack 2a.

When the power unit of the cell analyze facility is turned on, a program is read from an ROM, not shown, and is then loaded in the MPU 21 so as to initialize the system (ST41). Then, a protocol suitable for the measurement objective sample is selected and is set to the system. This operation is necessary because the sample processing method varies depending on the measurement objects. For example, there are developed the different reaction characteristics of the cells with respect to the monoclonal antibodies employed for the measurements, and hence the detector gain is respectively set for each of the photosensors 15a to 15d. In addition, there exist also various linkage types between the respective monoclonal antibodies and the fluorescent dye, the correction operation is hence also changed accordingly.

When the processing of ST42 is completed, the samle rack 2a is driven so as to locate the sample container 3 in which the sample to be first measured is contained to location directly below the sample sip or sip tube 4. Thereafter, like in the case of the step 23 of FIG. 11, the sample fluid is sipped such that the cells of the sample flow in a line through the flow channel 10a along a center axis thereof (ST43). The laser beam is irradiated onto each of the cells so as to measure the forward scattered light intensity $I_0$, the right angle scattered light intensity $I_{90}$, the green fluorescence intensity $I_g$, and the red fluorescence intensity $I_r$ (ST44).

In ST45, the MPU 21 produces a cytogram (FIG. 1) with the the forward scattered light intensity $I_0$ and the right angle scattered light intensity $I_{90}$ set as the ordinate and the abscissa, respectively and further generates histograms thereof (FIGS. 2a and 2b). The subsequent ST46 judges to determine whether or not a minimal point is detectable in the histogram of $I_{90}$.

If the sample is normal, three minimal points $p_1$, $p_2$, and $p_3$ can be detected in the $I_{90}$ histogram (refer to FIG. 2a for details of a case of lymphocyte subset analysis). In this case, control branches to ST49; whereas when the sample is abnormal and the system cannot detect any minimal point, the processing proceeds to ST47 so as to notify the abnormality to the operator. The report is effected through a display on the CRT 23 or by use of a voice or the like. In response thereto, the operator conducts a manual correction of the fraction (ST48) and then control is transferred to ST49.

In ST49 and ST50, like in the processing of ST5 to ST8 of FIG. 5, the minimal points $p_1$, $p_2$, and $p_3$ are detected in the histogram of $I_{90}$ so as to select and to collect data for which $I_{90}$ is between $p_1$ and $p_2$ from all the measured data associated with the sample. FIGS. 6a and 6b show histograms of $I_{90}$ and $I_0$ related to the data thus selected and collected. Furthermore, minimal points are extracted from the $I_0$ histogram of FIG. 6b so as to determine a final fraction B based on these minimal points (refer also to FIG. 1).

Figure 13:
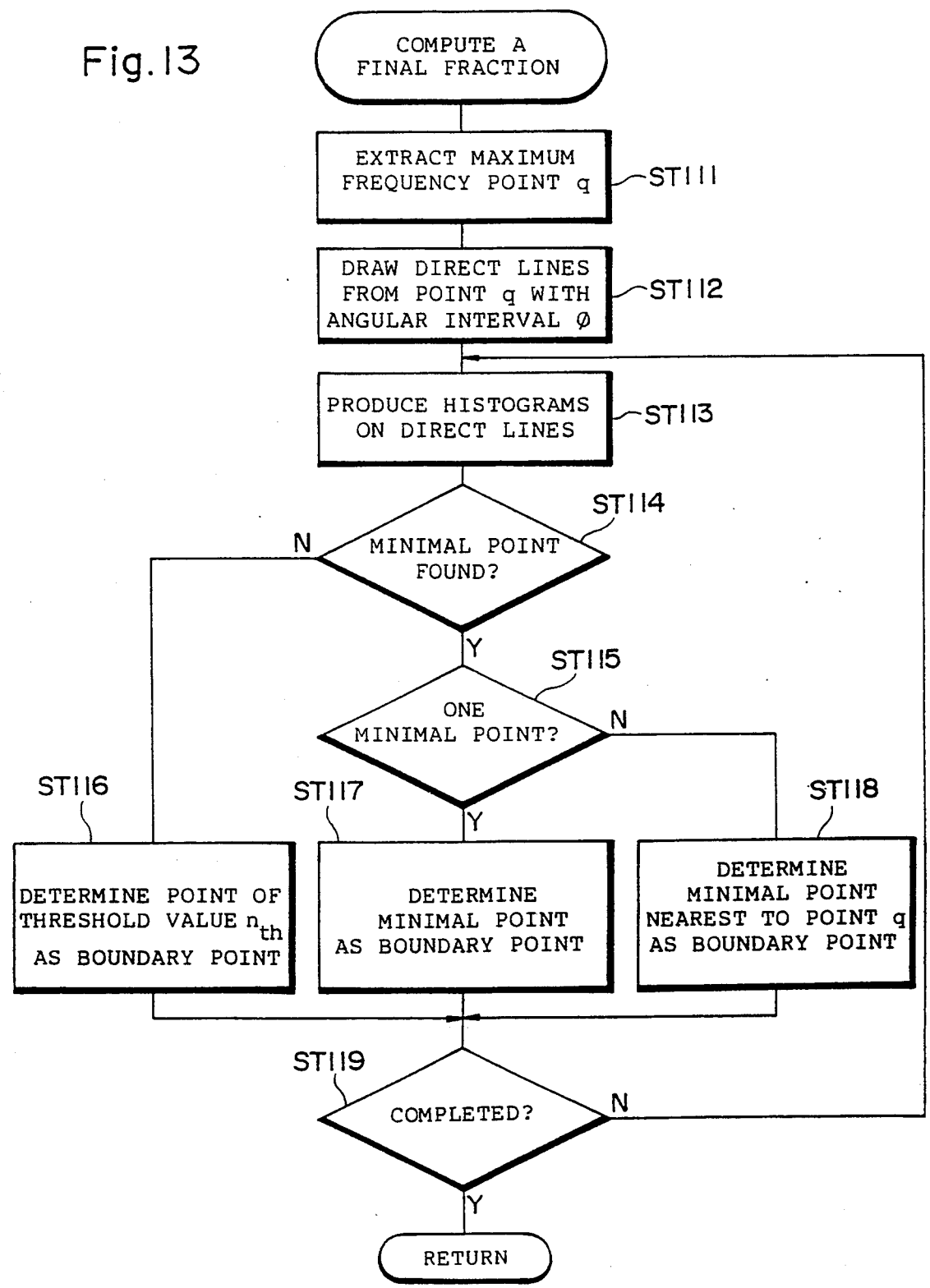
Figure 14:
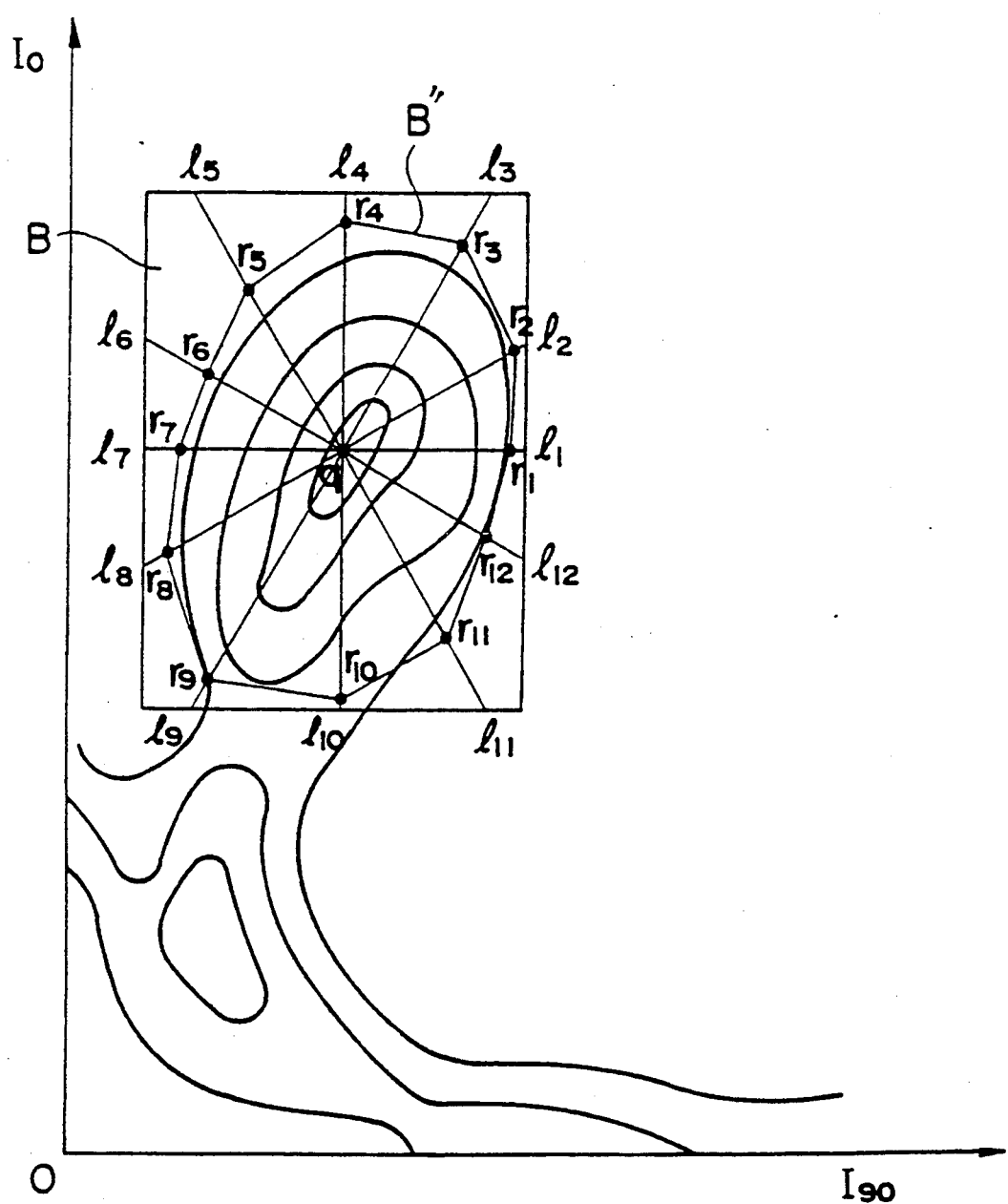

In the subsequent ST51, the data in the final segment thus determined in ST50 is processed to effect a computation of the final segment. Description will be given to the computation of the final segment or fraction with reference to FIG. 13. First, the maximum frequency point q is extracted from the data in the partition determined in ST50 (ST111). Thereafter, direct lines l are drawn from the point q with an angular inteval of $\Phi$ (ST112). For example, in a case of the lymphocyte subset analysis, as shown in FIG. 14, the maximum frequency point q is detected in the fraction B so as to produce direct lines $l_1$ to $l_{12}$ in a radial direction. The angular interval is not limited to 30°; furthermore, there may be employed unequal angular intervals to draw the direct lines.

Figure 15A:
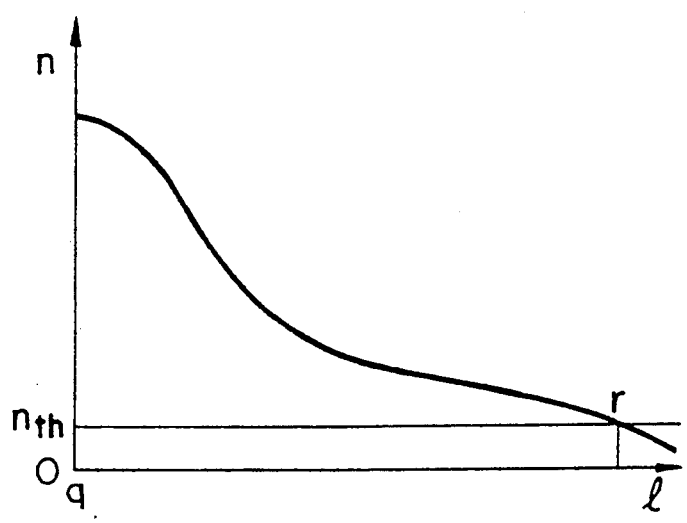
Figure 15B:
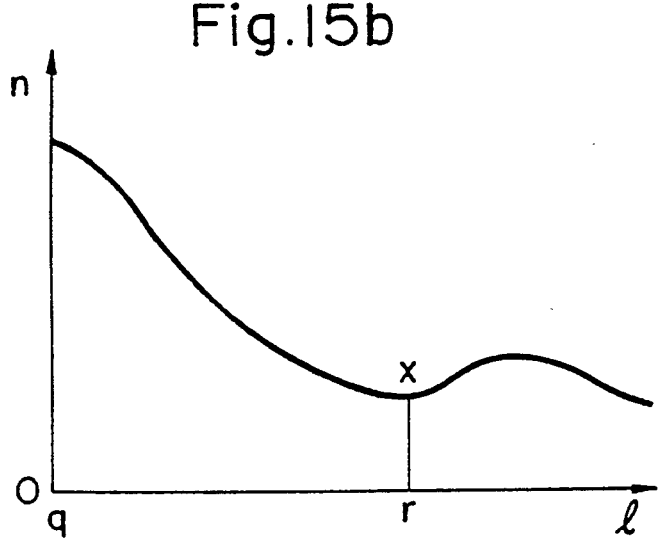
Figure 15C:
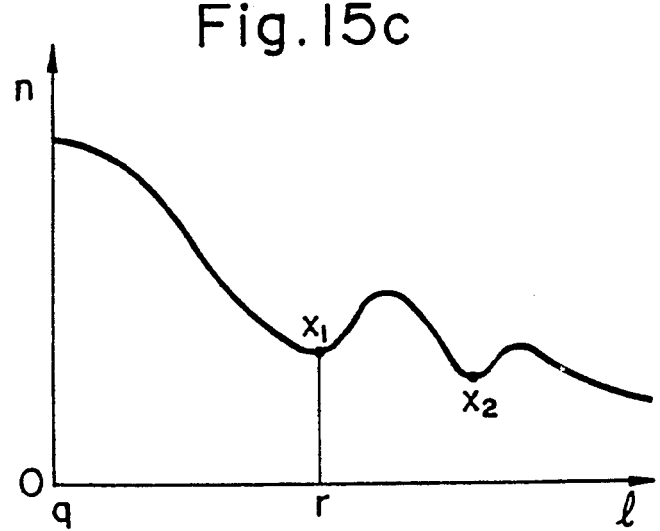
Figure 16:
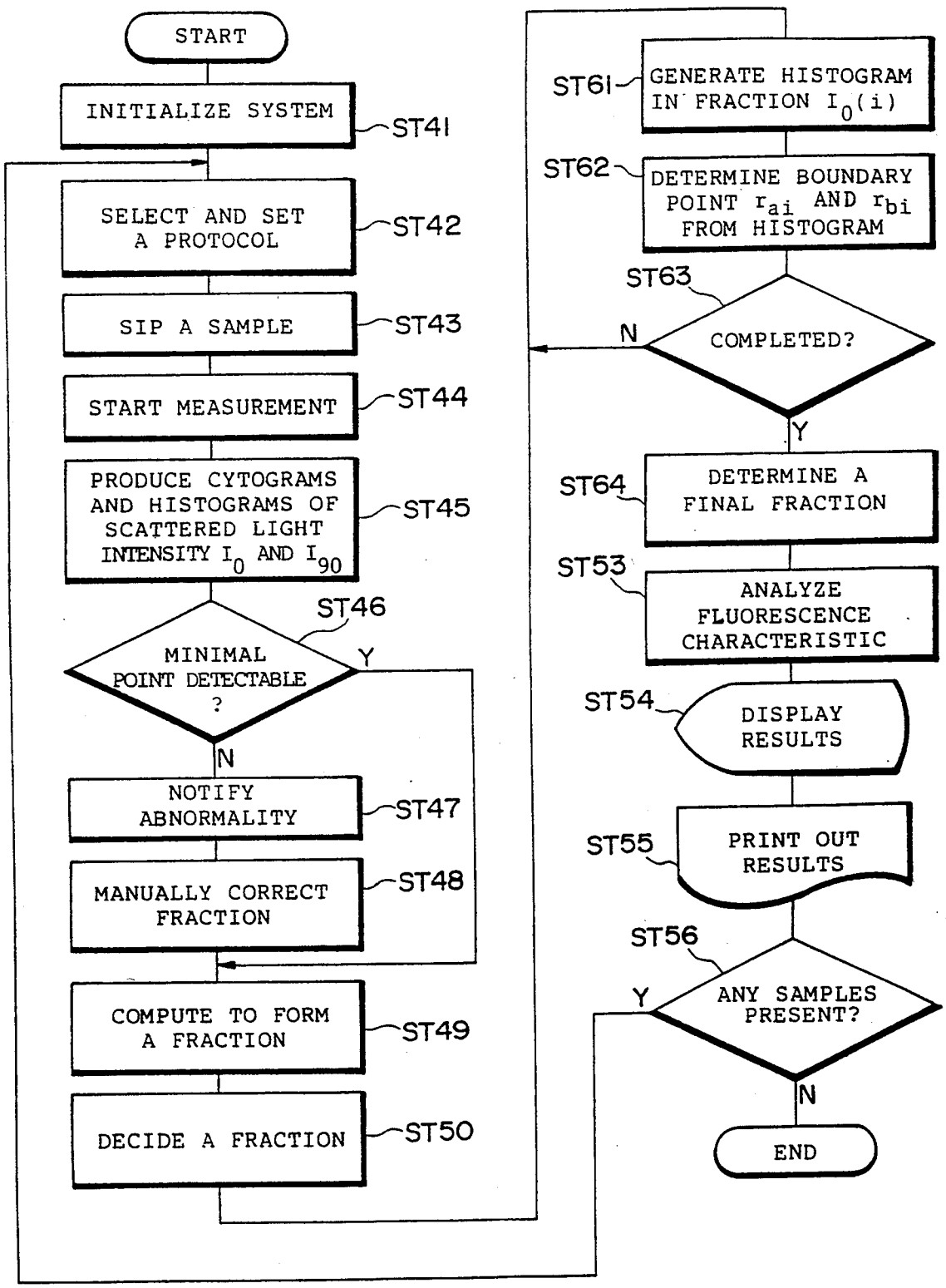

Next, histograms are generated on the respective direct lines $l_1$ to $l_{12}$ (ST113). FIGS. 15a, 15b, and 15c are schematic diagrams useful to explain examples of the histograms. Subsequently, judgement is conducted to determine whether or not minimal points can be extracted from the histograms obtained in ST113. If the judgement results in YES, control branches to ST115; whereas for a result of NO, the processing proceeds to ST116 (ST114). In ST115, judgement is further conducted to determine whether or not only a minimal point is extracted. If the judgement results in YES, control is passed to ST117; otherwise (when two or more minimal points are extracted), the processing proceeds to ST118.

FIG. 15a shows a case where the histogram does not include a minimal point. In this case, the processing proceeds to ST116 so as to set as a boundary point r a point where the histogram intersects the threshold value $n_{th}$. The diagram of FIG. 15b shows a case where a minimal point x is found. In this situation, control is transferred to ST117 so as to set the minimal point as the boundary point r. FIG. 15c shows a case where two minimal points $x_1$ and $x_2$ are detected. Under this condition, the proceeding proceeds to ST118 so as to set as the boundary point r the minimal which is nearest to the maximum frequency point q.

In ST119, the system judges to determine whether or not the boundary points are determined for all direct lines l. If the result is NO, processing proceeds to ST113 to generate a histogram for the next direct line; otherwise, control returns to the main routine of FIG. 12 so as to execute the processing of ST52. FIG. 14 shows the boundary points $r_1 \sim r_{12}$ which are associated with the respective direct lines $l_1$ to $l_{12}$ and which are obtained through the computation of the final fraction.

ST52 determines as the final fraction an area obtained by linking the boundary points $r_1 \sim r_{12}$ with direct lines, the points being determined in ST51. In the case of FIG. 14, an area B" drawn by linking with direct lines the boundary points $r_1$ to $r_{12}$ is determined as a final fraction. The final fraction B" is more suitable, as compared with the fraction B determined in ST50, for the distribution of the lymphocytes. In addition, as compared with the contour trace method, the processing time can be minimized.

The data belonging to the final segment obtained in ST52 is further subjected to fluorescence characteristic analysis (ST53). In the fluorescence characteristic analysis, for example, histograms are respectively created for the green fluorescence intensity and the red fluorescence intensity Ir so as to effect computations such as a calculation of positive ratios. The results of the fluorescence characteristic analysis are displayed on the CRT 23 (ST54) and are printed out on a print form by use of the printer (ST55).

ST56 judges to determine whether or not there exists any sample to be measured. If the judgement results in YES, the processing returns to ST42 so as to measure the next sample; otherwise, the measurement is finished.

Incidentally, the description above has been given of an example of the lymphocyte subset analysis; however, the present invention is not restricted by this example, namely, the present invention is broadly applicable also to analyses of populations of various cells (or particles like cells) such as red blood cell reticulocytes, and thrombocytes. Furthermore, the parameters are not limited to the four parameters including the forward scattered light intensity, the right angle scattered light intensity, the green fluorescence intensity, and the red fluorescence intensity. Moreover, the present invention is also applicable to a cell analyze apparatus employing the window method. In this case, the final fraction or segment is determined in the window.

It is to be understood that the processing of the final fraction computation and determination effected in ST51 and ST52 of FIG. 12 can also be applied to the fraction B' attained through the conversion processing of ST14 and ST15 of FIG. 5.

FIGS. 16 to 18b show a fourth embodiment according to the present invention. Also in this embodiment, there are directly used the configuration of FIGS. 4 or 10. Moreover, in the flowchart of FIG. 16, the same processing of the steps of FIG. 12 is assigned with the same reference numeral. Description will now be given of only the different points with respect to the third embodiment.

Figure 17:
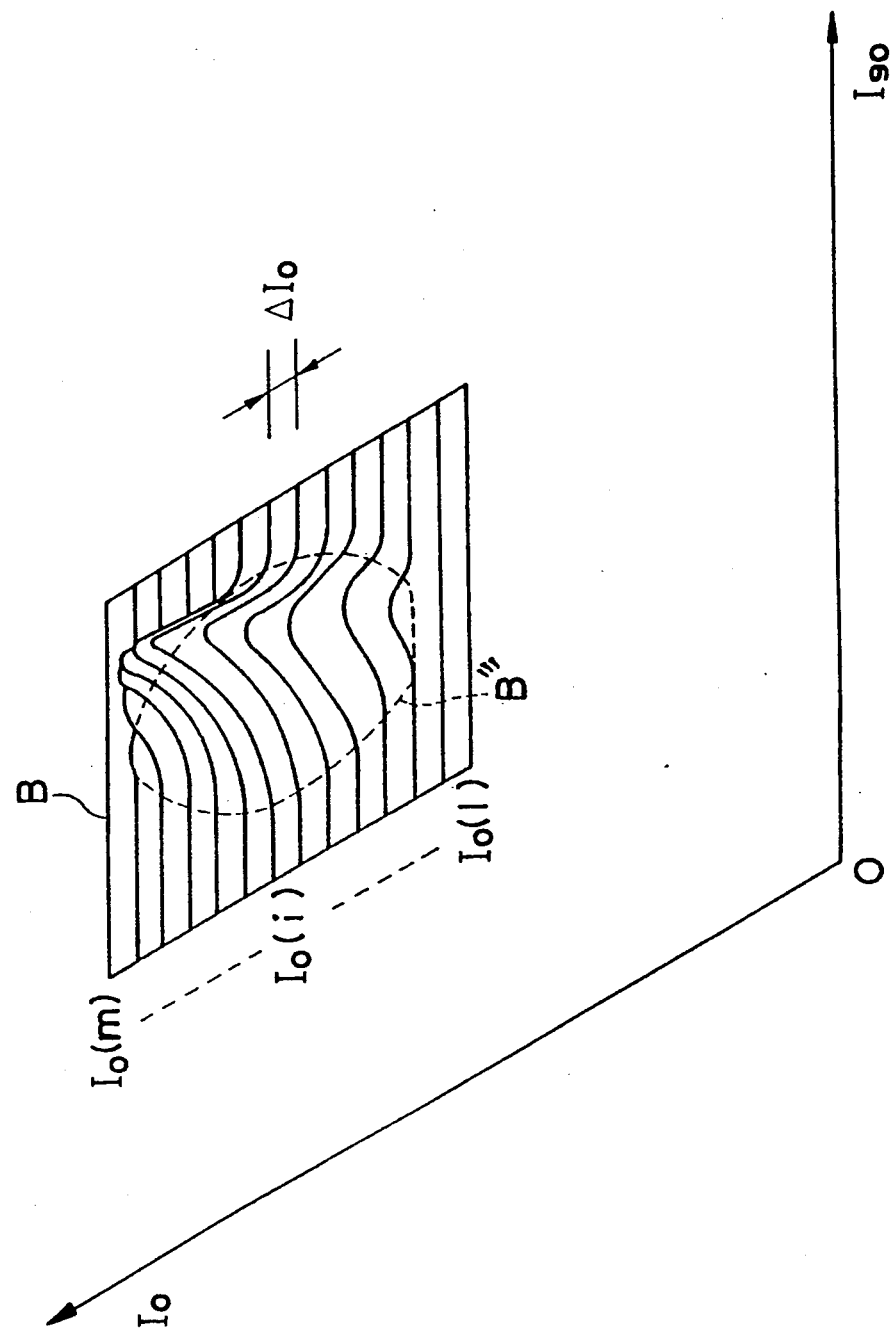
Figure 18A:
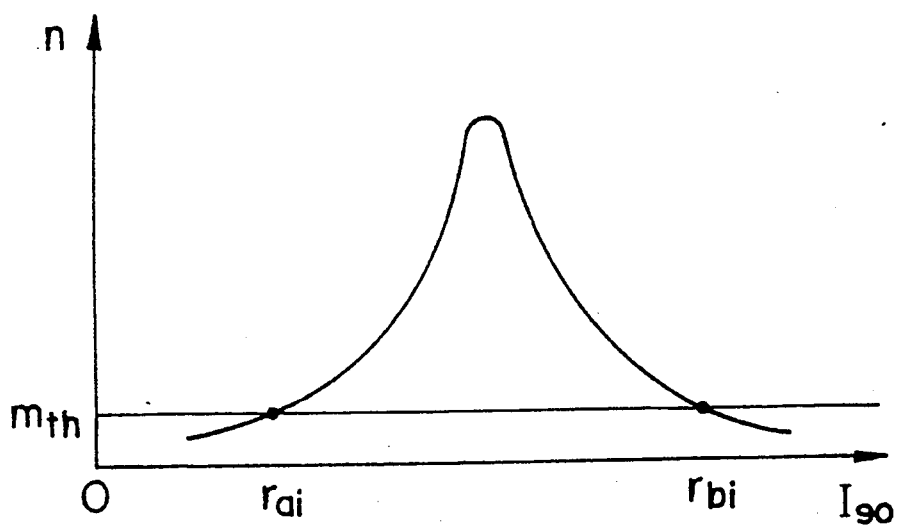
Figure 18B:
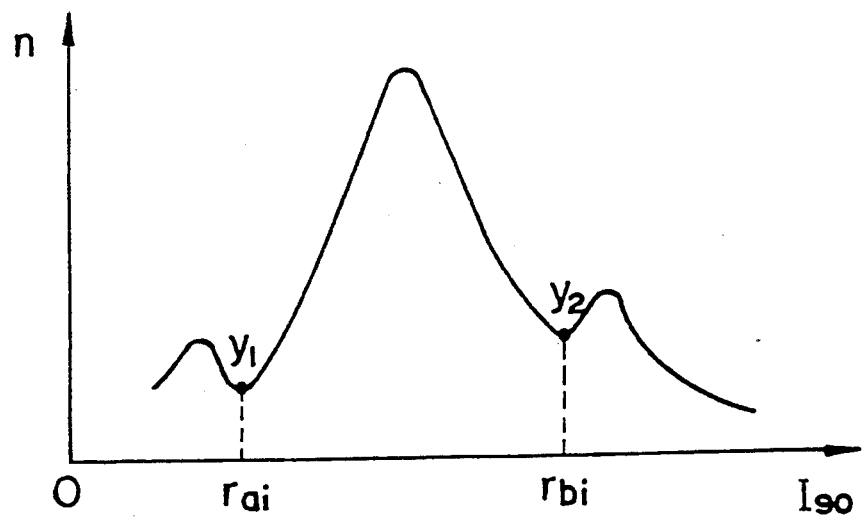

In ST61 following ST50, a histogram of the intensity of right angle scattered light $I_{90}$ is created on a line associatedd with the forward scattered light intensity $I_0(i)$ within the fraction B (refer to FIGS. 17, 18a, and 18b for details). ST62 then determines boundary points $r_{ai}$ and $r_{bi}$ on the produced histogram. In this operation, if the system cannot determine any minimal points in the histogram as shown in FIG. 18a, the points where the histogram intersects the predetermined threshold value $m_{th}$ are set as the boundary points and $r_{bi}$. Furthermore, as shown in FIG. 18b, if the histogram includes minimal points $y_1$ and $y_2$, these points are established as the boundary points. Naturally, it may also be possible to determine one of the two boundary points by use of the threshold value and the other one thereof depending on the minimal point. In a case where the histogram is entirely below the threshold value m th or where there cannot be detected any minimal point in the histogram, it is assumed that the boundary point is missing in this case.

In ST63, a check is carried out to determine whether or not the boundary points $r_{ai}$ and $r_{bi}$ are completely deteremined. If NO results, the processing returns to ST61 so as to similarly generate a histogram with respect to $I_0(i+1)$ obtained by incrementing $I_0(i)$ by $\Delta I_0$, thereby determining the boundary points (ST62). That is, in the fraction B, a histogram is produced for each of lines $I_0(l)$ to $I_0(m)$ drawn at an interval of $\Delta I_0$ so as to sequentially determine the boundary points.

If the judgement of ST63 results in YES, control branches to ST64 in which the boundary points $r_{ai}$ and $r_{bi}$ are sequentially linked with each other to obtain a final fraction B'''. The obtained final fraction B''' has a form which is more suitable for the lymphocyte distribution as compared with the fraction attained in ST50. Moreover, ST61 to ST63 can execute processing at a higher speed when compared with the case of the contour trace method.

In addition, a fluorescence characteristic analysis is accomplished on the data belonging to the final segment thus determined in ST64 (ST53). In the fluorescence characteristic analysis, histograms are respectively created for the green and red fluorescence intensity Ig and Ir and then the system conducts operations such as a positive ratio computation. The results of the fluorescence characteristic analysis are displayed on the CRT23 (ST54) and are printed out on a sheet of paper by means of the printer 24 (ST55).

It is to be appreciated that the decision processing of the final fraction B''' in ST61 to ST63 is also applicable to the segment B' obtained through the conversion processing of ST14 and ST15 of FIG. 5.

FIGS. 19 to 22 show a fifth embodiment of a cell analyze apparatus according to the present invention in which the threshold levels employed to execute the noise removal can be automatically adjusted.

Figure 19:
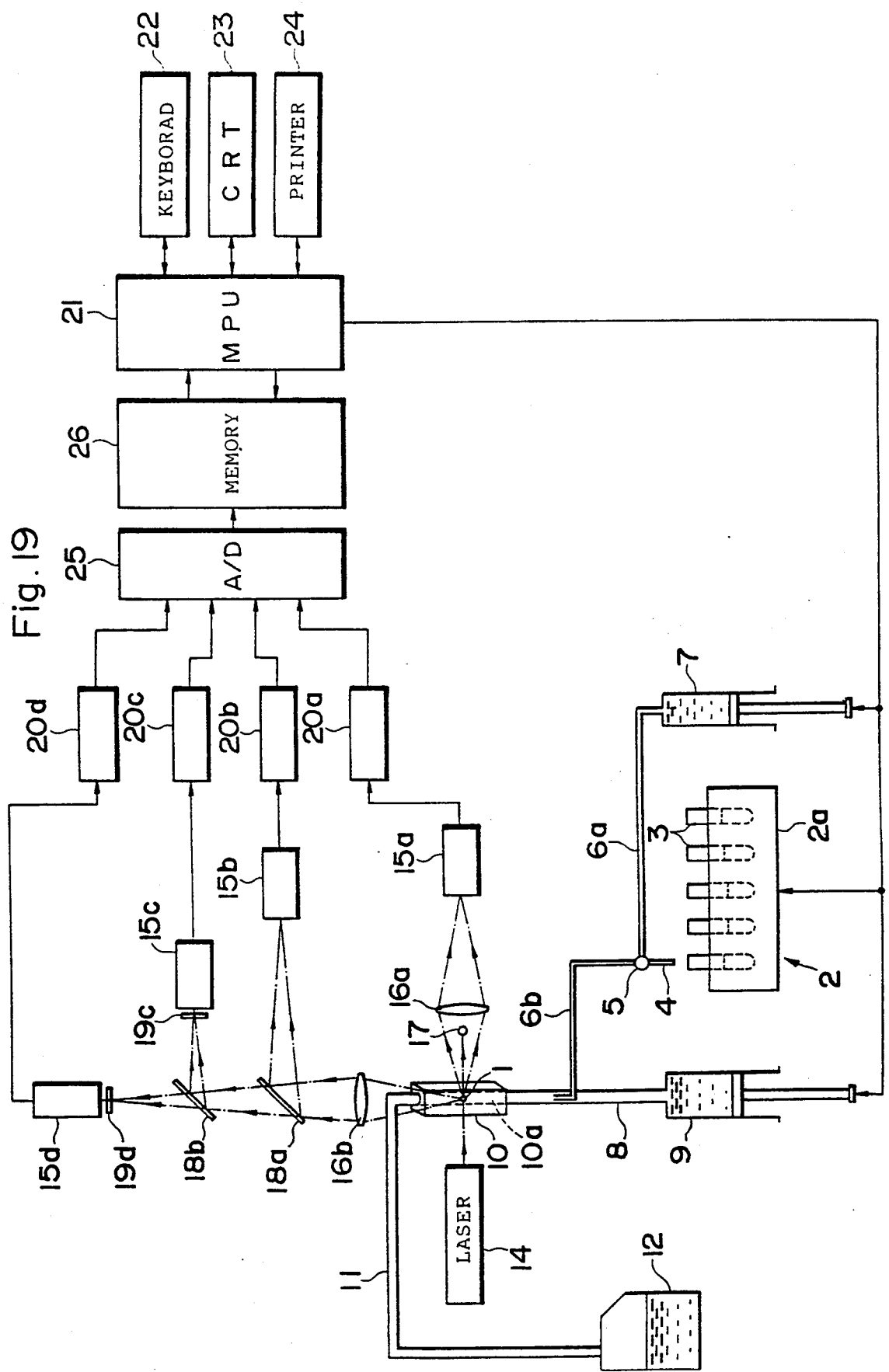

In the configuration of FIG. 19, the constituent elements equivalent to those of FIG. 10 are assigned with the same reference numerals and description thereof will be omitted.

The cell analyze equipment of the fifth embodiment includes a noise threshold circuit operating by use of hardware system similar to a device employed in the conventional apparatus. Furthermore, in order to assist the operation of the noise threshold circuit, there is applied noise threshold levels by use of so-called software system in acordance with the present invention. The noise threshold levels associated with the software is established depending on minimal points obtained from a histogram of the forward scattered light intensity $I_0$.

Figure 20:
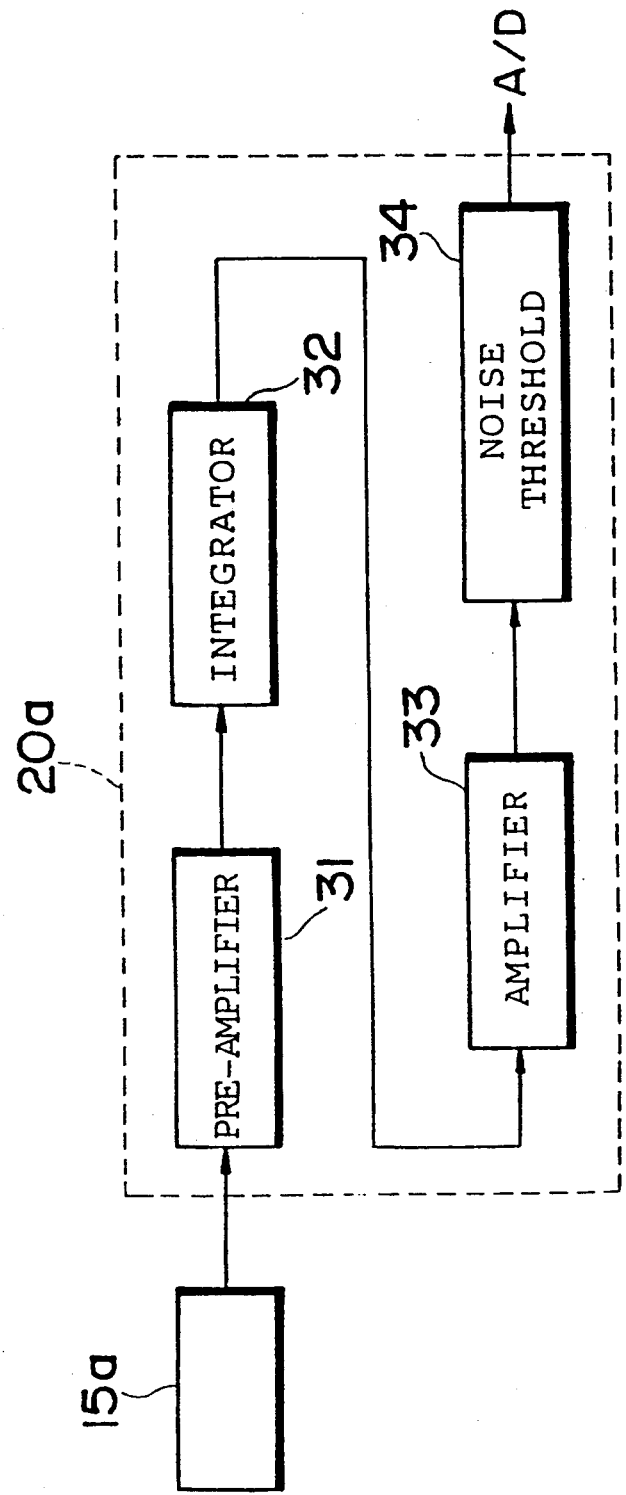

The configuration includes photosensors 15a to 15d to receive lights so as to produce light signals, which are respectively transferred for processing thereof to light signal processing circuits 20a to 20d such that the processed signals are fed to an analog-to-digital (A/D) converter 25 so as to be temporarily stored as digital signals in a memory 26. The light signal processing circuit 20a includes, as shown in FIG. 20, a preamplifier 31 for amplifying the light signal from the photosensor 15a, an integrator 32 for integrating an output produced from the pre-amplifier 31, an amplifier 33 for amplifying an output produced from the integrator 32, and a noise threshold circuit 34 for blocking a light signal component associated with a noise in the output from the amplifier 33. The other light signal processing circuits 20b to 20c are also consitituted in the similar fashion described above.

Figure 3A:
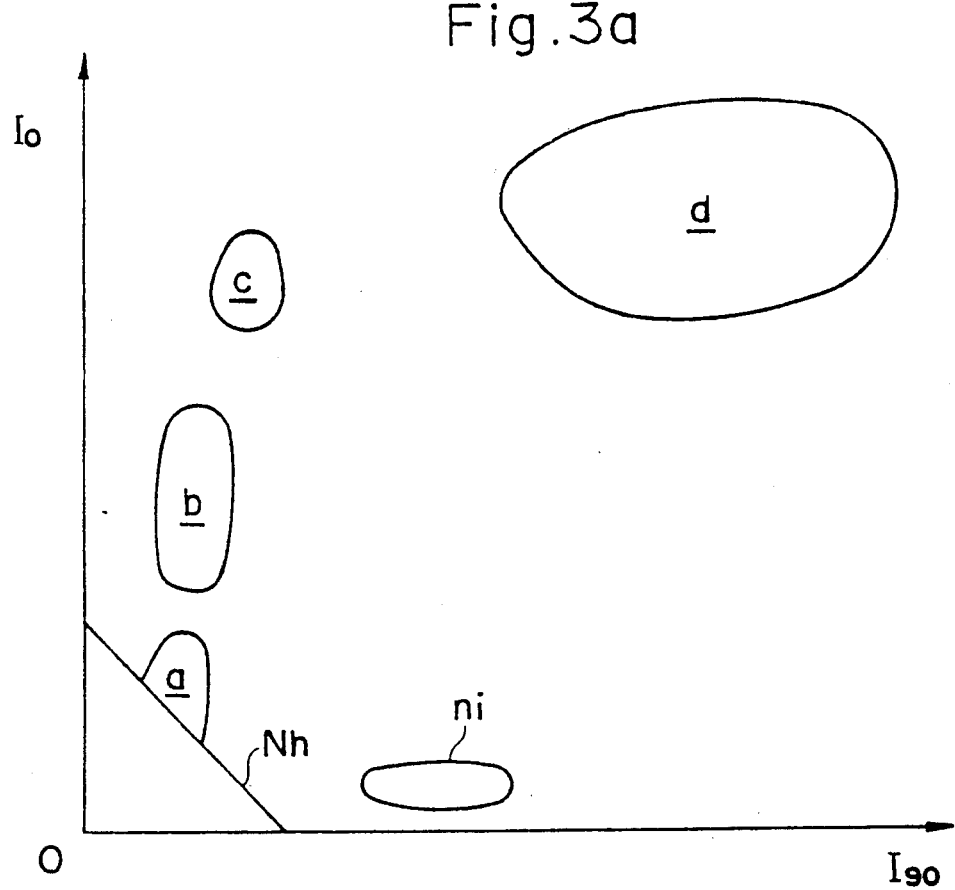
FIGS. 3a and 3b are graphs showing cytograms of the intensity respectively of forward scattered light and right angle scattered light useful to explain the noise threshold.

According to the cell analyzer of this embodiment, in each noise threshold circuit 34 of the signal processing circuits 20a and 20b, the system sets a noise threshold Nh, as shown in FIG. 3a, on a cytogram associated with the forward scattered light intensity $I_0$ and the right angle scattered light intensity $I_{90}$. The threshold Nh is set by means of hardware system and is fixed in this embodiment.

Data stored in the memory 26 is fed for processing thereof to the MPU 21. The MPU 21 develops various functions such as a function to create a histogram of the forward scattered light intensity $I_0$, a function to detect a minimal point p in the $I_0$ histogram, a function to correct the noise threshold Ns by use of the minimal point so as to remove the noise, a function to determine an analysis area or a fraction for the data thus obtained by removing the noise, a function to effect computations of data in the analysis area, and a function to control the auto-sampler 2, the sample pump 7, and the sheath pump 9.

Figure 21:
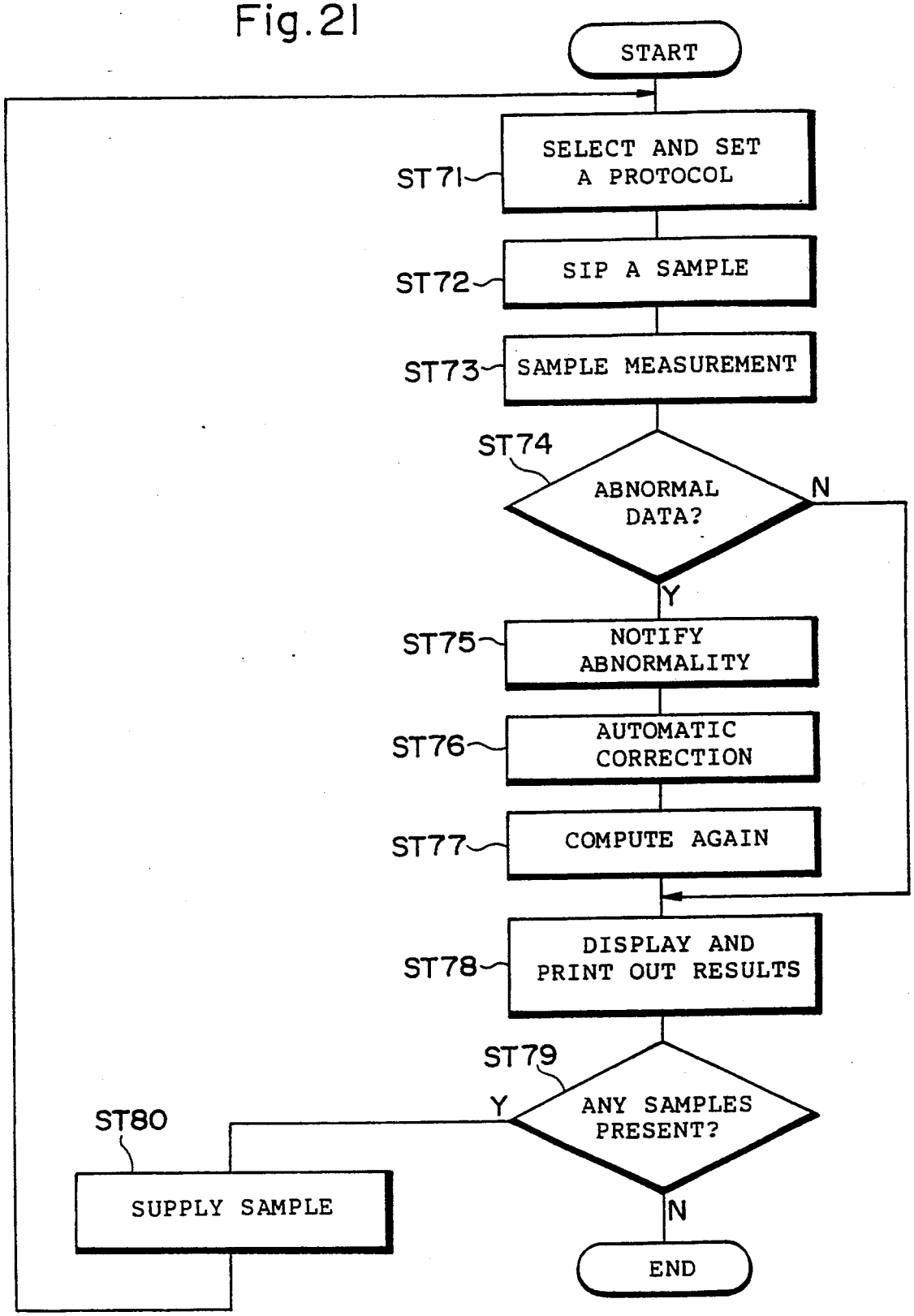

Referring next to FIG. 21, description will be given of the operation of the cell analyze apparatus of the embodiment 5.

Figure 11:
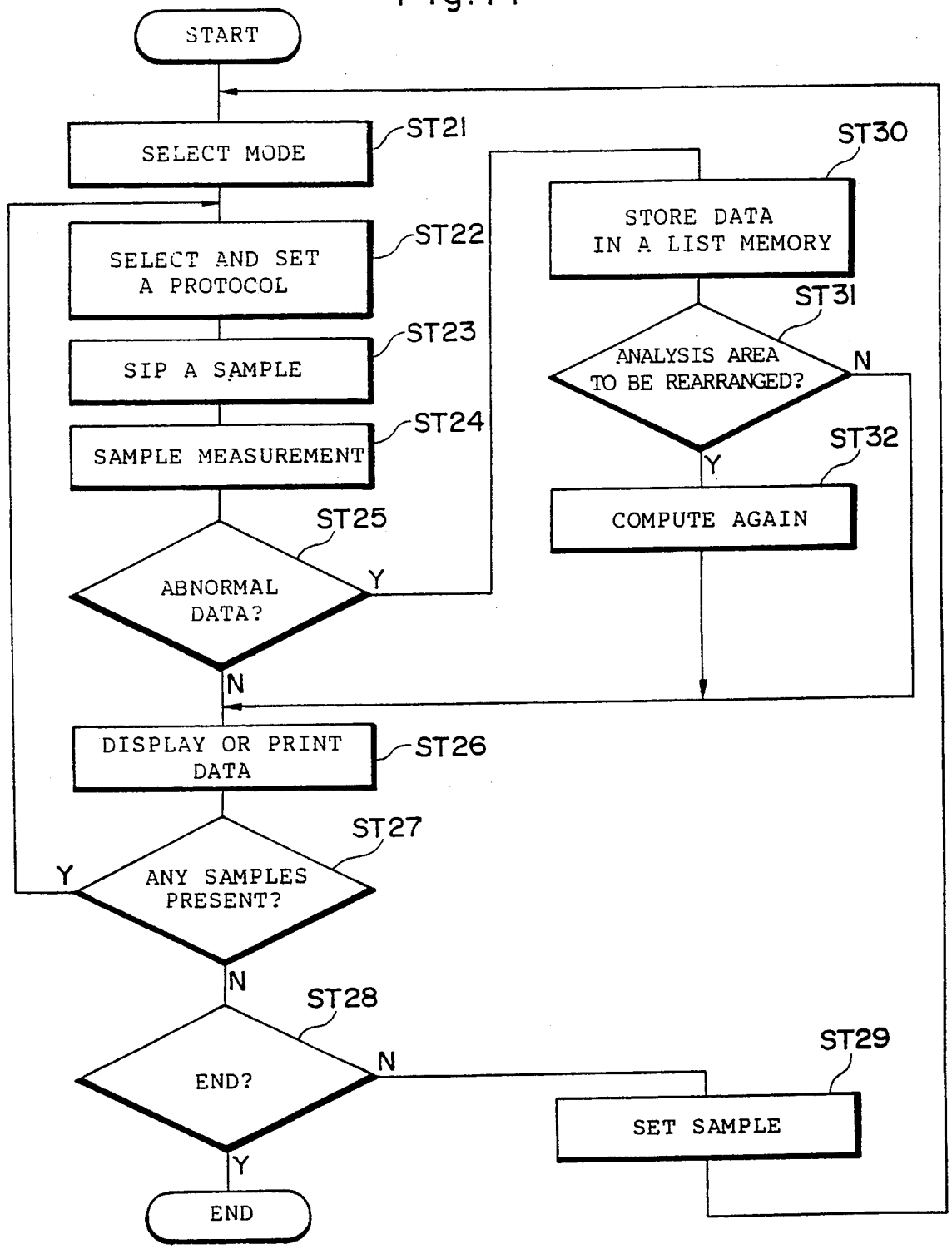

In the flowchart of FIG. 21, the processing of ST71 to ST73 is identical to that of ST22 to ST24 of FIG. 11.

In the measurement processing (ST73), for example, in a case of an analysis of leucocytes, the system produces a cytogram related to the forward scattered light intensity $I_0$ and the right angle scattered light $I_{90}$ intensity (refer to FIG. 3a for details). Thereafter, for example, an analysis region is established for the distribution of lymphocytes such that there are computed, for the data in the analysis area, an average intensity, the standard deviation (SD), and coefficient of variation (CV) so as to effect operations such as a comparison of the obtained data with reference values prepared in advance, thereby determining the normality or abnormality of the data (ST74). If the judgement results in YES, control is passed to ST75; otherwise (in the normal case), the processing branches to ST78.

Figure 3B:
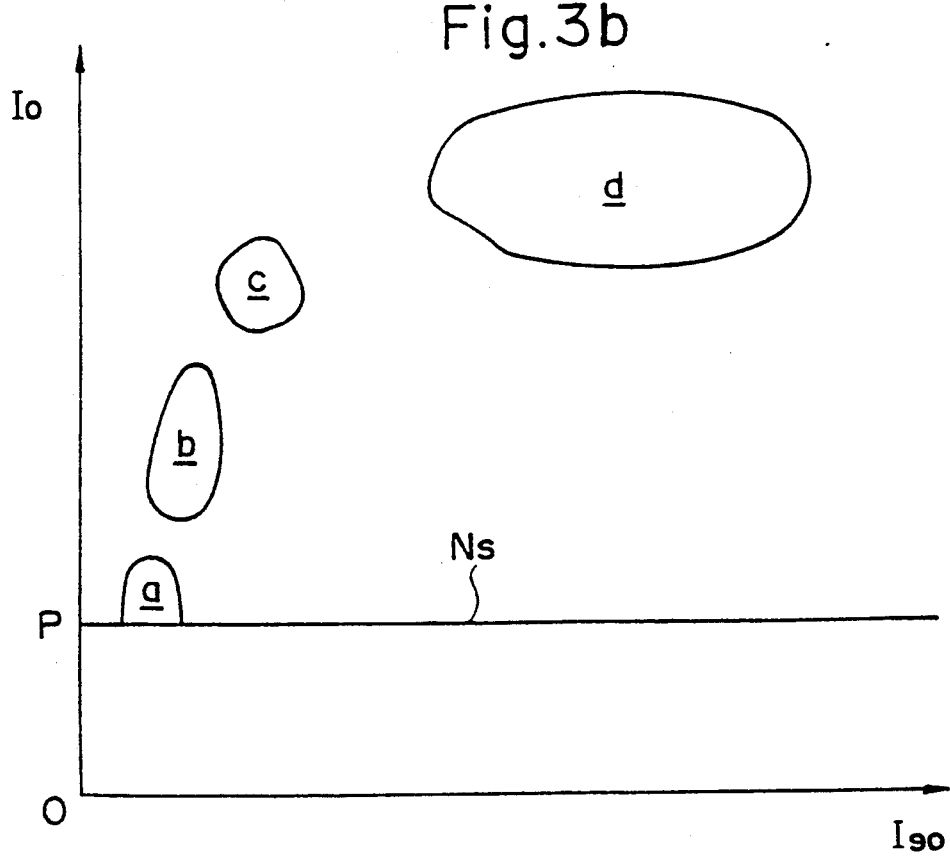

In ST75, the abnormal condition is reported to the operator, and in the subsequent ST76, the noise threshold and the analysis area are automatically corrected; thereafter, the system re-executes the computation in ST77. In FIG. 3a, the threshold Nh is set by use of the noise threshold circuit 34; however, it is impossible in some cases to remove the noise ni and other unnecessary signal components only by means of the noise threshold Nh. In order to overcome this difficulty, the MPU 21 effects a computation to set the threshold level Ns as shown in FIG. 3b, thereby conducting an automatic correction.

For setting the noise threshold level Ns, the system first detects a minimal point p, as shown in FIG. 22, from the histogram of the forward scattered light intensity $I_0$ (which is generated for the data prepared by removing the noise based on the noise threshold Nh). Since the portion for which $I_0$ is smaller than the minimal point p is related to a noise caused by ghost and dust, the noise threshold Ns is established as shown in FIG. 3b, thereby removing the unnecessary data from the data above. In the graph of FIG. 22, the portion exceeding the minimal point p represents the total number of leucocytes; consequently, if an analysis region is beforehand set for the lymphocytes, it is possible to determine an existence ratio or a present ratio of the lymphocytes in the leucocytes, which may be employed as an effective information item when a function of the leucocytes with respect to the immunity is to be examined.

In a case where there does not exist any abnormality as a result of ST74 or where the computation is executed again in ST77, control is transferred to ST78 so as to process data in a predetermined procedure, thereafter the results of the processing are displayed on the CRT 23 and are printed out on a print form by means of the printer 24. In ST79, a check is effected to determine whether ot not the specified samples also include any sample to be measured. If this judgement results in YES, the processing branches to ST80 in which the sample rack 2a is driven to locate the next sample to a position immediately below the sip tube 4 and then control returns to ST71. On the other hand, if the result of ST79 is NO, the system finishes the measurement.

Incidentally, the description above has been given of an example of blood cell analysis of a sample particularly, a sample of leucocytes; however it is to be understood that the present invention is also applicable to analyses of samples other than blood cells. In addition, the parameter associated with the setting of the noise threshold is not limited to the intensity of forward scattered light, namely, an arbitrary modification of the parameter is also possible.

While particular embodiments of the invention have been shown and described, it will be obvious to those skilled in the art that various changes and modifications may be made without departing from the present invention in its broader aspects.

We claim:

1. A cell analyze apparatus comprising:
   a flow cell through which a cell float fluid flows;
   a light source for irradiating a light beam onto cells flowing through said flow cell;
   cell light information detecting means for detecting, for each said cell irradiated by the light beam, cell light information with respect to a plurality of parameters;
   cell population subdividing means for detecting minimal points in histograms of cell light information obtained by said cell light information detecting means with respect to one or more parameters to subdivide a population of the cells in the cell float fluid into functions based on the minimal points;
   cell light information collecting means for collecting, based on one or more of the fractions produced by said cell population subdividing means, cell light information of an objective cell population from the cell light information attained by said cell light information detecting means;
   cell light information processing means for processing the cell light information of the objective cell population collected by said cell light information collecting means;
   output means for outputting results of the processing conducted by said cell light information processing means; and parameter converting means for converting said one or more parameters depending on a predetermined conversion expression, said cell population subdividing means detecting minimal points from histograms of the cell light information with respect to new parameters attained through a conversion achieved by said parameter converting means.

2. A cell analyze apparatus according to claim 1 wherein:

said cell light information collecting means includes a cell light information separating means, said cell light information separating means separating, from the cell light information detected by said cell light information detecting means, cell light information of a cell population belonging to one or more fractions with respect to a parameter, said cell light information collecting means collecting, from the separated cell light information, cell light information of a cell population belonging to a predetermined fraction with respect to other parameters.

3. A cell analyze apparatus according to claim 1 further including:

maximum frequency point extracting means for processing the cell light information of the objective cell population collected by said cell light information collecting means to extract a maximum frequency point on a cytogram of parameters associated with the fraction of the cell population;

direct line generating means for radially drawing direct lines from the maximum frequency point extracted by said maximum frequency point extracting means on the cytogram;

boundary point extracting means for extracting boundary points based on histograms on the respective direct lines produced by said direct line generating means; and second cell light information collecting means for linking the boundary points extracted by said boundary point extracting means to form a final fraction to collect cell light information of an objective cell population based on the final fraction.

4. A cell analyze apparatus according to claim 1 further including:

histogram generating means for processing the cell light information collected by said cell light information collecting means to attain, for each predetermined frequency of a parameter, a histogram of another parameter;

boundary point extracting means for extracting boundary points based in each histogram generated by said histogram generating means; and second cell light information collecting means for linking the boundary points extracted by said boundary point extracting means to form a final fraction to collect cell light information of an objective cell population based on the final fraction.

5. A cell analyze apparatus according to claim 1 further including:

histogram generating means for generating a histogram of cell light information with respect to at least a parameter of the cell light information detected by said cell light information detecting means;

minimal point detecting means for detecting a minimal point of the histogram created by said histogram generating means; and unnecessary information removal means for setting a noise threshold based on the minimal point detected by said minimal point detecting means to remove, by use of the noise threshold, unnecessary information included in the cell light information detected by said cell light information detecting means.

6. A cell analyze apparatus according to claim 1 further including:

sample supply means for sequentially sipping a plurality of samples to supply the sipped samples to said flow cell; and measurement condition setting means for setting to said cell light information processing means an optimal measurement condition depending on the sample to be supplied by said sample supply means.

7. A cell analyze apparatus comprising:

a flow cell through which a cell float fluid flows;

a light source for irradiating a light beam onto cells flowing through said flow cell;

cell light information detecting means for detecting, for each said cell irradiated by the light beam, cell light information with respect to a plurality of parameters;

cell population subdividing means for detecting minimal points in histograms of cell light information obtained by said cell light information detecting means with respect to one or more parameters to subdivide a population of the cells in the cell float fluid into fractions based on the minimal points;

cell light information collecting means for collecting, based on one or more of the fractions produced by said cell population subdividing means, cell light information of an objective cell population from the cell light information attained by said cell light information detecting means;

cell light information processing means for processing the cell light information of the objective cell population collected by said cell light information collecting means; and output means for outputting results of the processing conducted by said cell light information processing means, said cell light information collecting means having cell light information separating means, said cell light information separating means separating, from the cell light information detected by said cell light information detecting means, cell light information of a cell population belonging to one or more fractions with respect to a parameter, said cell light information collecting means collecting, from the separated cell light information, cell light information of a cell population belonging to a predetermined fraction with respect to other parameters.

8. A cell analyze apparatus comprising:

a flow cell through which a cell float fluid flows;

a light source for irradiating a light beam onto cells flowing through said flow cell;

cell light information detecting means for detecting, for each said cell irradiated by the light beam, cell light information with respect to a plurality of parameters;

cell population subdividing means for subdividing, based on one or more parameters obtained by said cell light information detecting means, a population of the cells in the cell float fluid into fractions;

first cell light information collecting means for collecting, based on one or more of the fractions produced by said cell population subdividing means, cell light information of an objective cell population from the cell light information attained by said cell light information detecting means;

cell light information processing means for processing the cell light information detected by said cell light information detecting means and the cell light information of the objective cell population collected by said first cell light information collecting means;

output means for outputting results of the processing conducted by said cell light information processing means;

Maximum frequency point extracting means for processing the cell light information of the objective cell population collected by said first cell light information collecting means to extract a maximum frequency point on a cytogram of parameters associated with the fraction of the cell population;

direct line generating means for radially drawing direct lines from the maximum frequency point extracted by said maximum frequency point extracting means on the cytogram;

boundary point extract means for extracting boundary points based on histograms of the respective direct lines produced by said direct line generating means; and second cell light information collecting means for linking the boundary points extracted by said boundary point extracting means to form a final fraction to collect cell light information of an objective cell population based on the final fraction.

9. A cell analyze apparatus according to claim 8, wherein said boundary point extracting means extracts as boundary points where the histogram intersects a threshold value or the minimal points of the histograms.

10. A cell analyze apparatus comprising:
a flow cell through which a cell float fluid flows;
a light source for irradiating a light beam onto cells flowing through said flow cell;
cell light information detecting means for detecting, for each said cell irradiated by the light beam, cell light information with respect to a plurality of parameters;
cell population subdividing means for subdividing, based on one or more parameters obtained by said cell light information detecting means, a population of the cells in the cell float fluid;
first cell light information collecting means for collecting, based on one or more fractions of the fractions produced by said cell population subdividing means, cell light information of an objective cell population from the cell light information detected by said cell light information detecting means;
cell light information processing means for processing the cell light information detected by said cell light information detecting means and the cell light information of the objective cell population collected by said first cell light information collecting means;
output means for outputting results of the processing conducted by said cell light information processing means;
histogram generating means for processing the cell light information collected by said first cell light information collecting means to attain, for each predetermined frequency of a parameter, a histogram of other parameters;
boundary point extracting means for extracting boundary points based on each histogram generated by said histogram generating means; and
second cell light information collecting means for linking the boundary points extracted by said boundary point extracting means to form a final fraction to collect cell light information of an objective cell population based on the final fraction.

11. A cell analyze apparatus according to claim 10, wherein said boundary point extracting means extracts as boundary points where the histogram intersects a threshold value or the minimal points of the histograms.

12. A cell analyze apparatus comprising:
a flow cell through which a cell float fluid flows;
a light source for irradiating a light beam onto cells flowing through said flow cell;
cell light information detecting means for detecting, for each said cell irradiated by the light beam, cell light information with respect to a plurality of parameters;
cell light information discriminating means for discriminating cell light information of an objective cell population from the cell light information detected by said cell light information detecting means;
cell light information processing means for processing the cell light information detected by said cell light information detecting means and the cell light information discriminated by said cell light information discriminating means;
output means for outputting results of the processing conducted by said cell light information processing means;
histogram generating means for generating a histogram of cell light information with respect to at least a parameter of the cell light information detected by said cell light information detecting means;
minimal point detecting means for detecting a minimal point of the histogram created by said histogram generating means; and
unnecessary information removal means for setting a noise threshold based on the minimal point detected by said minimal point detecting means to remove, by use of the noise threshold, unnecessary information included in the cell light information detected by said cell light information detecting means.

13. A cell analyze apparatus comprising:
a flow cell through which a cell float fluid flows;
a light source for irradiating a light beam onto cells flowing through said flow cell;
cell light information detecting means for detecting, for each said cell irradiated by the light beam, cell light information with respect to a plurality of parameters;
cell light information discriminating means for discriminating cell light information of an objective cell population from the cell light information detected by said cell light information detecting means;
cell light information processing means for processing the cell light information detected by said cell light information detecting means and the cell light information discriminated by said cell light information discriminating means;

output means for outputting results of the processing conducted by said cell light information processing means;

sample supply means for sequentially sipping a plurality of samples to supply the sipped samples to said flow cell; and measurement condition setting means for setting to said cell light information processing means an optimal measurement condition depending on the sample to be supplied by said sample supply means.

* * * * *